United States Patent
Yanai

(10) Patent No.: US 7,160,242 B2
(45) Date of Patent: Jan. 9, 2007

(54) BLOOD PUMP SYSTEM

(75) Inventor: Masamichi Yanai, Nakai-machi (JP)

(73) Assignee: Terumo Kabushiki Kaisha, Tokyo (JP)

(*) Notice: Subject to any disclaimer, the term of this patent is extended or adjusted under 35 U.S.C. 154(b) by 505 days.

(21) Appl. No.: 10/671,543

(22) Filed: Sep. 29, 2003

(65) Prior Publication Data

US 2004/0064012 A1  Apr. 1, 2004

(30) Foreign Application Priority Data

Sep. 30, 2002  (JP) .............................. 2002-286646

(51) Int. Cl.
*A61N 1/362* (2006.01)
*A61M 1/10* (2006.01)

(52) U.S. Cl. ...................... 600/16; 623/3.13
(58) Field of Classification Search ............ 600/16–18; 623/3.13–3.15; 128/899
See application file for complete search history.

(56) References Cited

U.S. PATENT DOCUMENTS

| 4,778,445 A | 10/1988 | Hubbard et al. |
| 4,781,525 A | 11/1988 | Hubbard et al. |
| 5,725,357 A * | 3/1998 | Nakazeki et al. ............. 417/18 |
| 6,142,752 A | 11/2000 | Akamatsu et al. |
| 6,623,420 B1 * | 9/2003 | Reich et al. ................... 600/17 |
| 6,866,625 B1 * | 3/2005 | Ayre et al. ..................... 600/16 |

FOREIGN PATENT DOCUMENTS

WO  WO 01/72352 A2  10/2001

OTHER PUBLICATIONS

Yuhki A, Hatoh E, Nogawa M, Miura M, Shimazaki Y, Takatani S. "Detection of Suction and Regurgitation of the Implantable Centrifugal Pump Based on the Motor Current Waveform Analysis and Its Application to Optimization of Pump Flow." Artificial Organs, 1999. 23(6): 532-537.*

Kikugawa D. "Motor Current Waveforms as an Index for Evaluation of Native Cardiac Function During Left Ventricular Support with a Centrifugal Pump." Artificial Organs, 2001. 15(9): 703-708.*

* cited by examiner

Primary Examiner—Robert E. Pezzuto
Assistant Examiner—Tammie K. Heller
(74) Attorney, Agent, or Firm—Buchanan Ingersoll & Rooney PC

(57) ABSTRACT

A blood pump system includes a housing having an inlet port and an outlet port, a rotor rotated in the housing for pumping blood, and a motor for rotating the rotor. The blood pump system includes a motor current measuring function, and a backflow detecting function for detecting a backflow of blood by use of the motor current value continuously measured by the motor current measuring function.

14 Claims, 17 Drawing Sheets

BLOOD PUMP SYSTEM

BACKGROUND OF THE INVENTION

The present invention relates to a blood pump system for pumping blood as a continuous flow.

In recent years, development of continuous flow type blood pumps as artificial heart units has been conducted energetically. A general example of continuous flow type blood pump is the one of the type in which an impeller is rotated by a motor to thereby pump blood. Another example is a so-called axial flow pump in which a shaft is rotated by a motor to thereby pump blood. For measuring the blood flow rate in these pumps, there may be considered the following two methods:

(1) To attach a flow rate sensor.

(2) To calculate the flow rate from information on the motor.

The method of (1) is advantageous in that accurate flow rate measurement can be achieved, while the method of (2) is advantageous in that it is needless to provide a flow rate sensor and, hence, it is possible to reduce the apparatus in size and to reduce power consumption. Therefore, an apparatus of the type of (2) is more desirable.

In the method of (2), the flow rate of the pump is calculated, for example, from the rotational speed of the motor, the motor current, or the like. Taking a motor speed constant control (generally, a motor rotational frequency fixing control is conducted) as an example, the relationship between the motor current value and the pump flow rate at a flow rate of not less than 0 is a monotonous increase relationship, which makes it possible to calculate the pump flow rate from the motor current value. In this case, the pump system stores a flow rate operation expression, and the flow rate is calculated from an actually measured motor rotational speed and an actually measured motor current or the like by use of the operation expression.

As an system of the type (2) above, a centrifugal fluid pump system is disclosed in U.S. Pat. No. 6,142,752.

In the publication, there is disclosed the centrifugal fluid pump system in which a controller stores either flow rate-related data preliminarily obtained through measurement of the relationships between the motor current of the fluid pump system, the motor rotational speed and the flow rate or relational expression data calculated from the related data, and has a flow rate calculation function for calculating the flow rate by use of the motor current value, the motor rotational speed, the relational expression data, and the fluid viscosity calculated by a fluid viscosity calculating function.

In the case of pumping blood by a pump, it is necessary to prevent a backflow of the blood. Where a blood pump system is used as a left ventricular assist device, a backflow of blood is generated, for example, for the following reason. There is a period in which the aortic pressure is higher than the left ventricle pressure on the side of a living organism. For example, in the case where rotary pump assists pumping function from left ventricle to aorta, a backflow occurs if the pump head in this period is low. Such a backflow in the blood pump corresponds to the condition where the pump is out of function in the period.

In the system shown in the above-mentioned publication, a favorable calculation of the flow rate (flow rate) is possible under normal conditions. However, in a negative-flow-rate zone (the conditions for backflow), it is impossible to arithmetically calculate, or detect, the backflow by use of the flow rate operation expression which is prepared for a positive-flow-rate zone.

SUMMARY OF THE INVENTION

It is an object of the present invention to provide a blood pump system capable of detecting a backflow without provision of a flow meter.

In order to attain the above object, according to the present invention, there is provided a blood pump system which includes a housing having an inlet port and an outlet port, a rotor rotated in the housing for pumping blood, and a motor for rotating the rotor, the blood pump system including a motor current measuring function, and a backflow detecting function for detecting a backflow of blood by use of the motor current value continuously measured by the motor current measuring function.

With the blood pump system according to the present invention, it is possible to detect a backflow of blood without provision of a flow meter.

The blood pump system may include alarm means which is operated when it is determined by the backflow detecting means that a backflow is present. In this case, it is possible to inform the user of the generation of the backflow detected.

The blood pump system may include a rotational speed control function for increasing the rotational speed of the rotor when it is determined by the backflow detecting function that a backflow is present. In this case, it is possible to improve the backflow generation condition.

BRIEF DESCRIPTION OF THE DRAWINGS

The above and other objects, features and advantages of the present invention will become apparent from the following description and appended claims, taken in conjunction with the accompanying drawings, wherein:

DETAILED DESCRIPTION OF THE PREFERRED EMBODIMENTS

Now, one embodiment of the blood pump system according to the present invention will be described.

Figure 1:
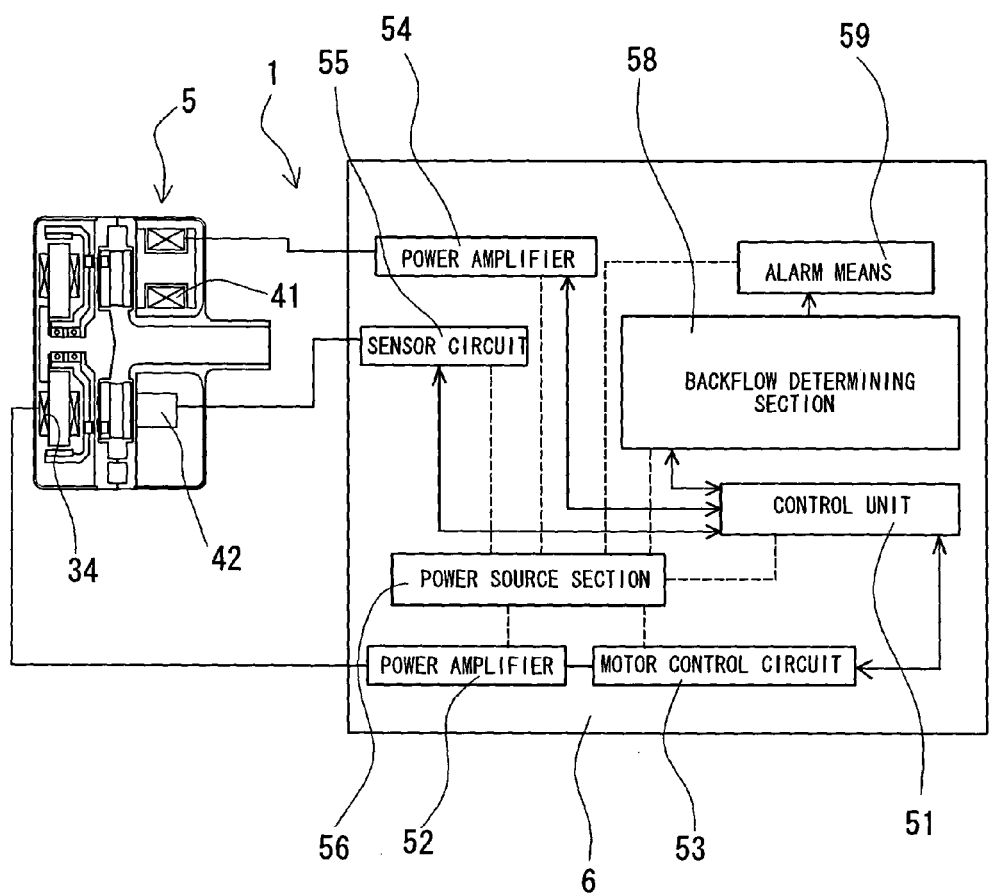
FIG. 1 is a block diagram of one embodiment of a blood pump system according to the present invention.
Figure 2:
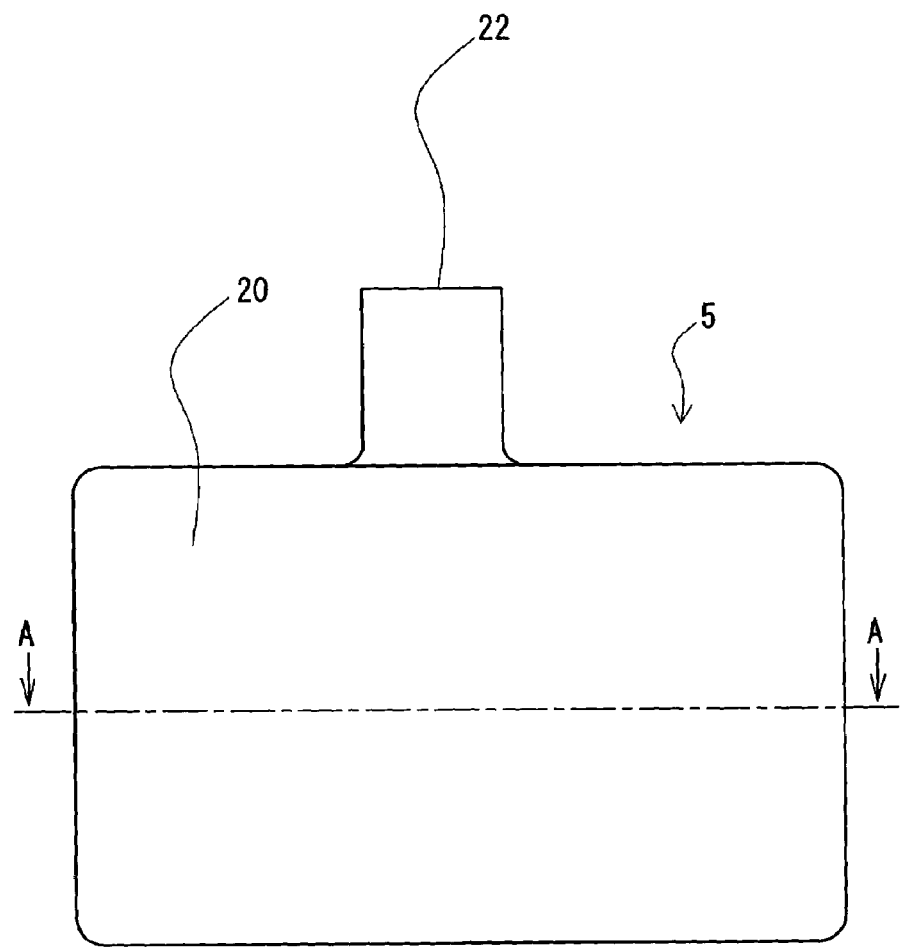
FIG. 2 is a front view of one example of a blood pump system main body portion used in the blood pump system according to the present invention.
Figure 3:
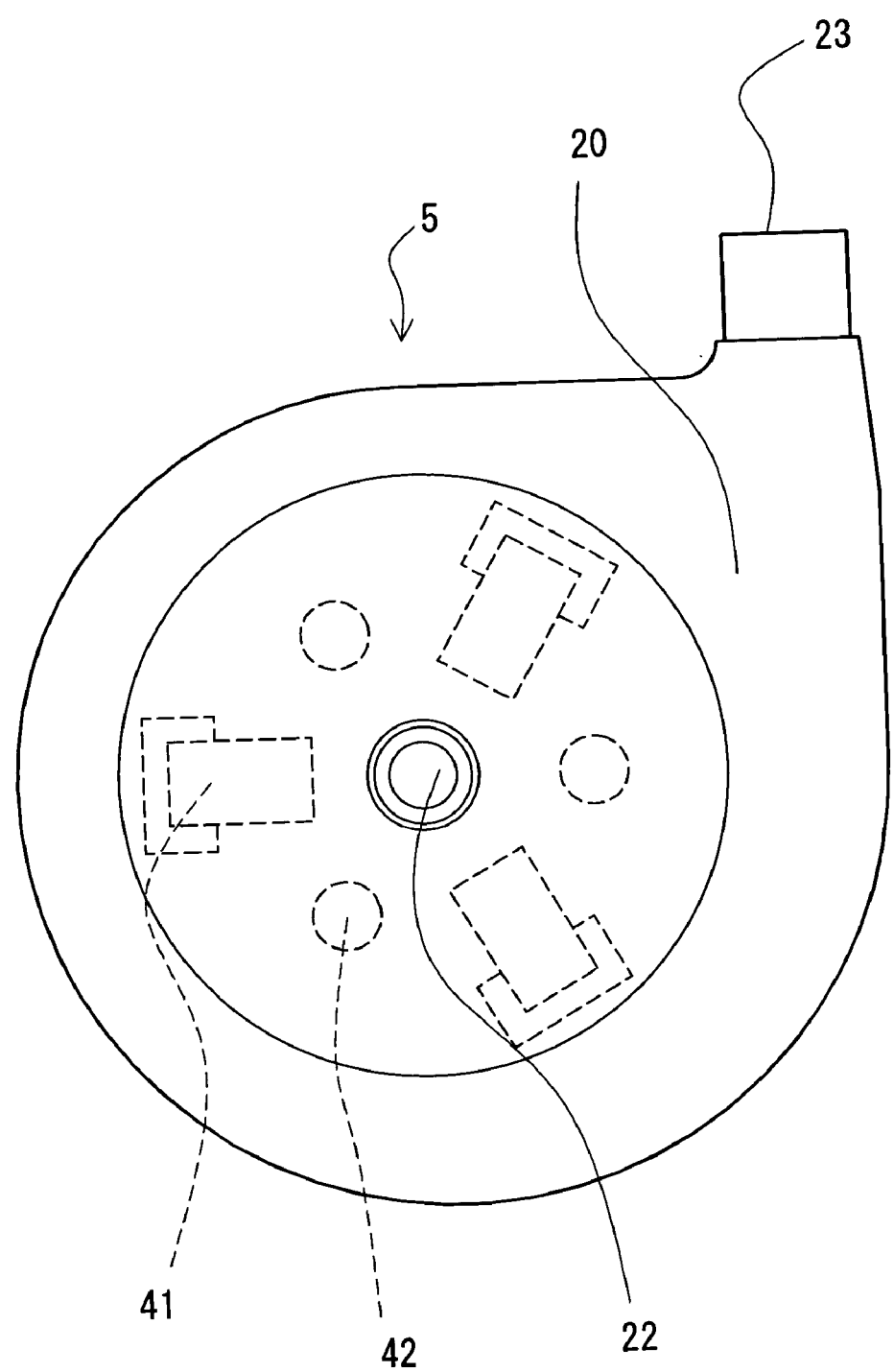
FIG. 3 is a plan view of the blood pump system main body portion shown in FIG. 2.
Figure 4:
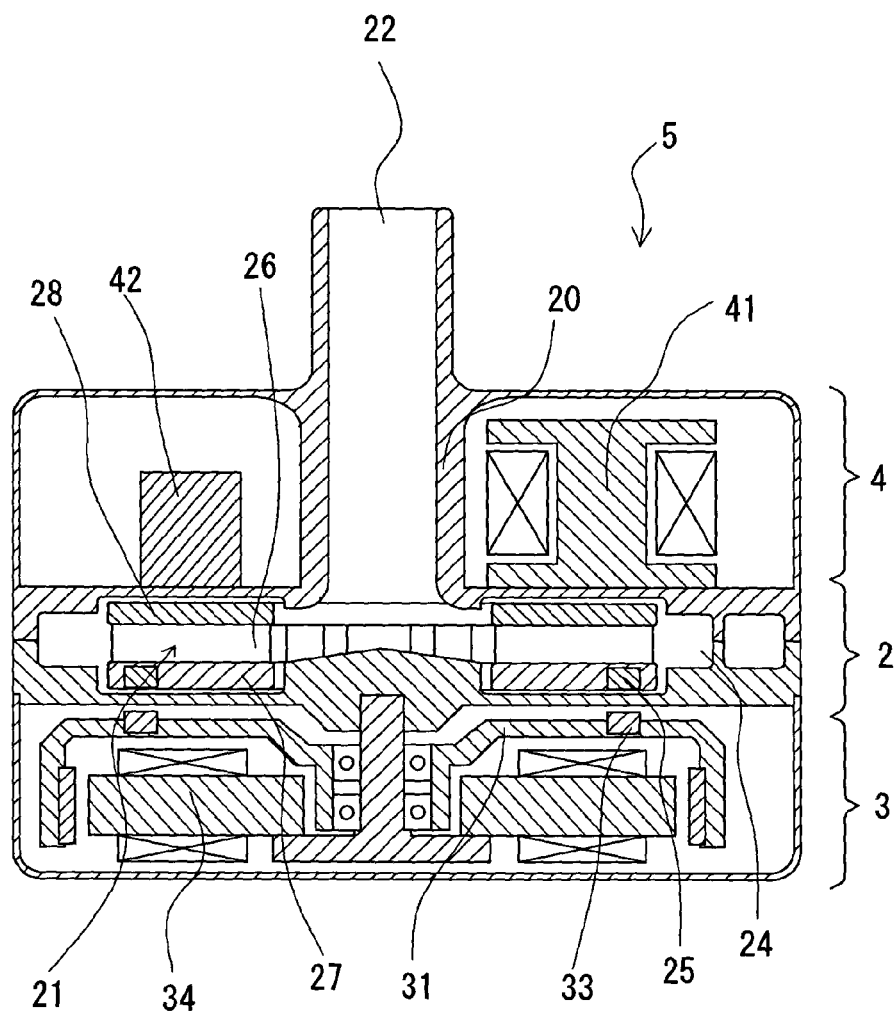
FIG. 4 is a vertical sectional view of the blood pump system main body portion of the embodiment shown in FIG. 2.
Figure 5:
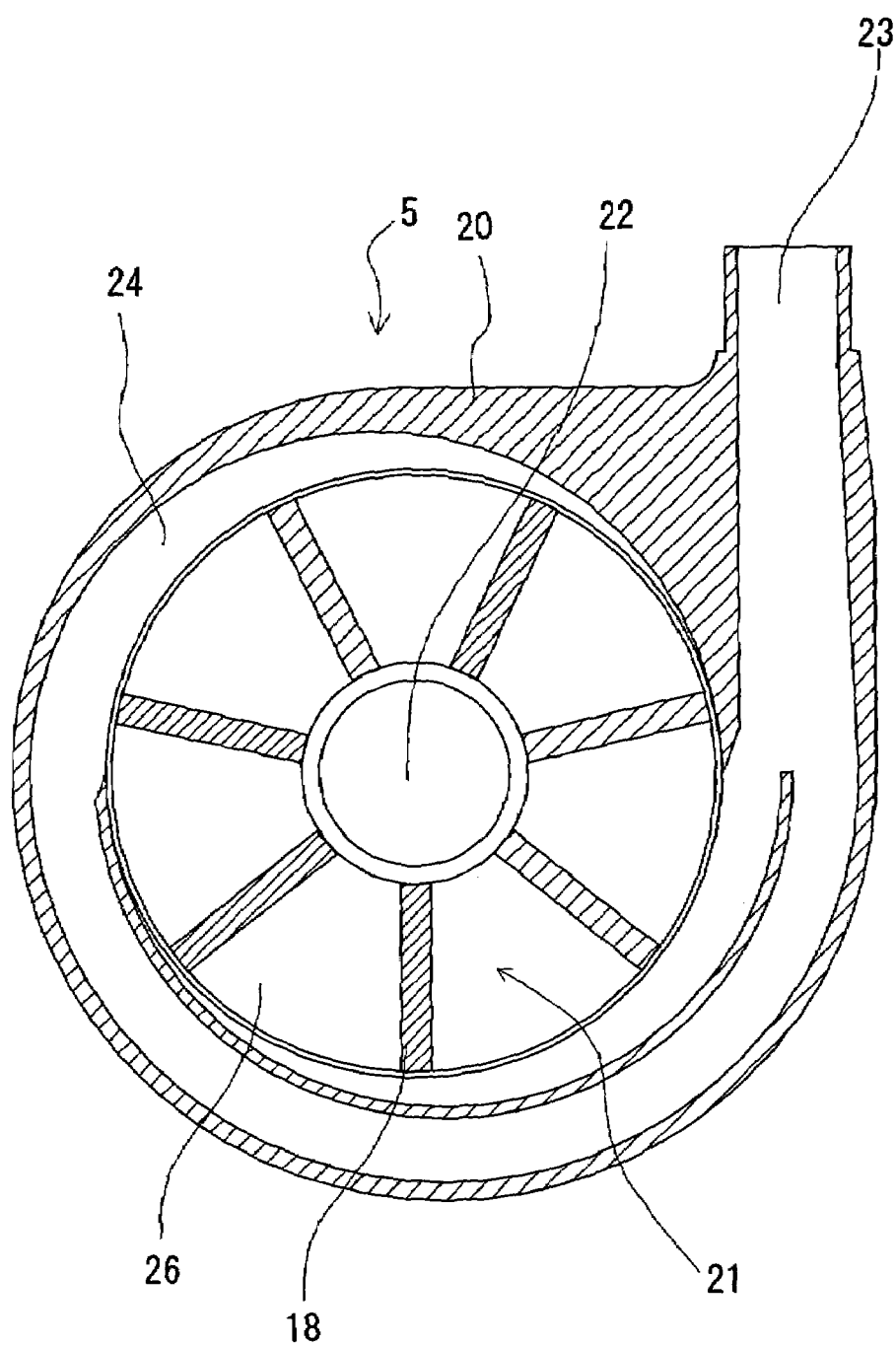
FIG. 5 is a sectional view taken along line A—A of FIG. 2.

FIG. 1 is a block diagram of one embodiment of the blood pump system according to the present invention. FIG. 2 is a front view of one example of a blood pump system main body portion used in the blood pump system according to the present invention. FIG. 3 is a plan view of the blood pump system main body portion shown in FIG. 2. FIG. 4 is a vertical sectional view of the blood pump system main body portion according to the embodiment shown in FIG. 2. FIG. 5 is a sectional view taken along line A—A of FIG. 2.

The blood pump system 1 according to the present invention comprises a housing 2 having an inlet port 22 and an outlet port 23, a rotor 21 rotated in the housing 2 for pumping blood, and a motor 34 for rotating the rotor 21. The blood pump system 1 comprises a motor current measuring function, and a backflow detecting function for detecting a backflow of blood by use of a motor current value continuously measured by the motor current measuring function.

In addition, the blood pump system 1 preferably does not comprise any direct flow rate detecting means.

The embodiment shown in the figures corresponds to an application of the blood pump system of the present invention to a centrifugal pump system.

The blood pump system 1 in this embodiment comprises a housing 20 having the inlet port 22 and the outlet port 23, an impeller 21 as the rotor rotated in the housing 20 so as to pump blood by centrifugal force upon rotation thereof, and the motor 34 for rotating the impeller 21.

The blood pump system 1 according to the embodiment shown in FIGS. 1 to 5 comprises the housing 20 having the inlet port 22 and the outlet port 23, a centrifugal pump unit 2 having the impeller 21 comprising a magnetic member 25 therein and being rotated in the housing 20 so as to pump blood by centrifugal force upon rotation thereof, a rotor 31 comprising a magnet 33 for attracting the magnetic member 25 of the impeller 21 of the centrifugal pump unit 2, an impeller rotational torque generating section 3 comprising the motor 34 for rotating the rotor 31, and an impeller position control section 4 comprising an electromagnet 41, wherein the impeller 21 is rotated in the housing 20 without any contact.

Incidentally, the blood pump system according to the present invention is not limited to the above-mentioned type in which the impeller is rotated without any contact. For example, the blood pump system is applicable to the type in which an impeller is joined to a shaft of a motor and is rotated by the rotation of the motor. In addition, the blood pump system according to the present invention is not limited to the above-mentioned centrifugal blood pump system but may be an axial flow type blood pump system.

As shown in FIGS. 2 to 6, the blood pump system main body portion 5 in this embodiment comprises the housing 20 having an inlet port 22 and an outlet port 23, the centrifugal pump unit 2 having the impeller 21 rotated in the housing 20 so as to pump blood by centrifugal force upon rotation thereof, the impeller rotational torque generating section (non-control type magnetic bearing component section) 3 for the impeller 21, and the impeller position control section (control type magnetic bearing component section) 4 for the impeller 21.

As shown in FIG. 4, the impeller 21 is held at a predetermined position inside the housing 20 by the functions of the non-control type magnetic bearing component section 3 and the control type magnetic bearing component section 4, and normally is rotated without making contact with the inside surface of the housing 20.

The housing 20 comprises the inlet port 22 and the outlet port 23, and is formed of a non-magnetic material. The housing 20 is provided therein with a blood chamber 24 which is communicated with the inlet port 22 and the outlet port 23. The housing 20 contains the impeller 21. The inlet port 22 is so provided as to project substantially vertically from the neighborhood of the center of the top surface of the housing 20. The outlet port 23 is so provided as to project in a tangential direction from a side surface of the housing 20, which is formed in a substantially cylindrical shape, as shown in FIGS. 3 and 5.

As shown in FIG. 5, the impeller 21 in a circular disk shape with a through-hole in the center thereof is contained in the blood chamber 24 formed inside the housing 20. As shown in FIG. 4, the impeller 21 comprises an annular plate-like member (lower shroud) 27 forming a lower surface, a center-opened annular plate-like member (upper shroud) 28 forming an upper surface, and a plurality of (for example, seven) vanes 18 formed between the annular plate-like members 27, 28. As a result, a plurality of (seven) blood passages 26 partitioned by adjacent ones of the vanes 18 are formed between the lower shroud and the upper shroud. As shown in FIG. 5, each of the blood passages 26 is communicated with the center opening of the impeller 21, and extends from the center opening of the impeller 21 to the outer circumferential edge of the impeller 21, with its width gradually increasing. In other words, each of the vanes 18 is formed between the adjacent blood passages 26. Incidentally, in this embodiment, the individual blood passages 26 and the individual vanes 18 are provided at regular angular intervals and in substantially the same shapes, respectively.

As shown in FIG. 4, a plurality of (for example, twenty-four) first magnetic members 25 (permanent magnets; driven magnets) are embedded in the impeller 21. In this embodiment, the first magnetic members 25 are embedded in the lower shroud 27. The magnetic members 25 (permanent magnets) thus embedded are provided for ensuring that the impeller 21 is attracted to the side opposite to the inlet port 22 by permanent magnets 33 provided in the rotor 31 of the impeller rotational torque generating section 3 which will be described later and that a rotational torque is transmitted from the impeller rotational torque generating section.

In addition, with a certain number of magnetic members 25 embedded, as in this embodiment, it is possible to secure a sufficient magnetic coupling with the rotor 31 which will be described later. The shape of the magnetic members 25 (permanent magnets) is preferably circular. Alternatively, the magnetic member 25 may be one obtained by dividing a ring-shaped magnet into a plurality of poles (for example, twenty-four poles), in other words, a set of a plurality of small magnets arranged in a ring shape, with opposite poles alternately arranged.

Besides, the impeller 21 comprises a second magnetic member 28 provided as the upper shroud itself or in the upper shroud. In this embodiment, the whole of the upper shroud is formed of the magnetic member 28. The magnetic member 28 is provided for attracting the impeller 21 to the side of the inlet port 22 by the electromagnet 41 of the impeller position control section which will be described later. As the material of the magnetic member 28, a magnetic stainless steel or the like is used.

The impeller position control section 4 and the impeller rotational torque generating section 3 constitute a non-contact type magnetic bearing. The impeller 21 is attracted in opposite directions, whereby the impeller 21 inside the housing 20 is stably held in an appropriate position without making contact with the inside surface of the housing 20, and is rotated inside the housing 20 without any contact.

As shown in FIG. 4, the impeller rotational torque generating section 3 comprises the rotor 31 contained in the housing 20, and the motor 34 for rotating the rotor 31. The rotor 31 comprises a plurality of permanent magnets 33 provided in a surface on the side of the liquid pump unit 2. The center of the rotor 31 is fixed to a rotary shaft of the motor 34. The permanent magnets 33 are provided in plurality and at regular angular interval, so as to correspond to the configuration (the number and the arrangement positions) of the permanent magnets 25 of the impeller 21.

The impeller rotational torque generating section 3 is not limited to the above-mentioned one comprising the rotor and the motor but may be, for example, one composed of a plurality of stator coils for attracting the permanent magnets 25 of the impeller 21 and for driving the latter to rotate.

As shown in FIGS. 3 and 4, the impeller position control section 4 comprises a plurality of fixed electromagnets 41 for attracting the magnetic members 28 of the impeller 21, and a position sensor 42 for detecting the position of the magnetic members 28 of the impeller 21. Specifically, the impeller position control section 4 comprises the plurality of electromagnets 41 and a plurality of position sensors 42, which are contained in the housing 20. The plurality of (three) electromagnets 41 and the plurality of (three) position sensors 42 of the impeller position control section 4 are provided at regular angular intervals, respectively, and the electromagnets 41 and the position sensors 42 are also provided at a regular angular interval therebetween. The electromagnet 41 is composed of an iron core and a coil. In this embodiment, three electromagnets 41 are provided. The number of the electromagnets 41 is three or more; for example, the number may be four. By providing three or more electromagnets 41 and adjusting the electromagnetic forces thereof by use of detection results obtained by the position sensors 42, it is possible to balance the forces in the direction of the rotational axis (z-axis) of the impeller 21 and to control the moments around the x-axis and y-axis which are orthogonal to the rotational axis (z-axis).

The position sensor 42 detects the spacing between the electromagnet 41 and the magnetic member 28, and the detection output is sent to a control unit 51 of a control mechanism (or controller) 6 for controlling the current or voltage applied to the coil of the electromagnet 41. In addition, even if a radial force due to gravity or the like is exerted on the impeller 21, the impeller 21 is held in the center of the housing 20 because the shearing forces of the magnetic fluxes between the permanent magnets 25 of the impeller 21 and the permanent magnets 33 of the rotor 31 and the shearing forces of the magnetic fluxes between the electromagnets 41 and the magnetic member 28 act on the impeller 21.

As shown in FIG. 1, the control mechanism 6 comprises a power amplifier 52 and a motor control circuit 53 for the motor 34 for magnetic coupling, a power amplifier 54 for the electromagnets 41, a sensor circuit 55 for the sensors 42, a sensor output monitoring unit (not shown) for monitoring the sensor outputs, a control unit 51, a power source section 56, a backflow determining section 58, and alarm means 59. In addition, the control mechanism 6 comprises a motor current monitoring function. To be more specific, a motor current value measured by a motor current measuring function possessed by the motor control circuit 53 is sent to the control unit 51, is subjected to analog-to-digital conversion, and the resulting digital signal is sent to a sequential backflow determining section 58. Then, the backflow determining section 58 determines the presence or absence of generation of a backflow, by use of the motor current value sequentially inputted. When it is determined by the backflow determining section 58 that a backflow is present, the alarm means 59 is operated to inform the user of the generation of the backflow. The alarm means is preferably sound-issuing means. The sound-issuing means is preferably a buzzer.

Further, the control unit 51 comprises a function of designating a motor rotational speed to the motor control circuit 53. Therefore, the motor and the impeller are rotated according to the motor rotational speed designated by the control unit 51. Besides, in this embodiment, the motor rotational speed designated in the control unit 51 is sent also to the backflow determining section 58.

The control mechanism 6 is not limited to the one of the above-described type but may be one comprising a motor rotational speed detector (not shown) electrically connected to the motor control circuit. In that case, the controller 6 comprises a motor rotational speed monitoring function. The motor rotational speed detected by the motor rotational speed detector is inputted to the control unit. Then, the motor rotational speed is outputted from the control unit to the backflow determining section.

Next, the backflow determining function of the backflow determining section 58 will be described.

Figure 11:
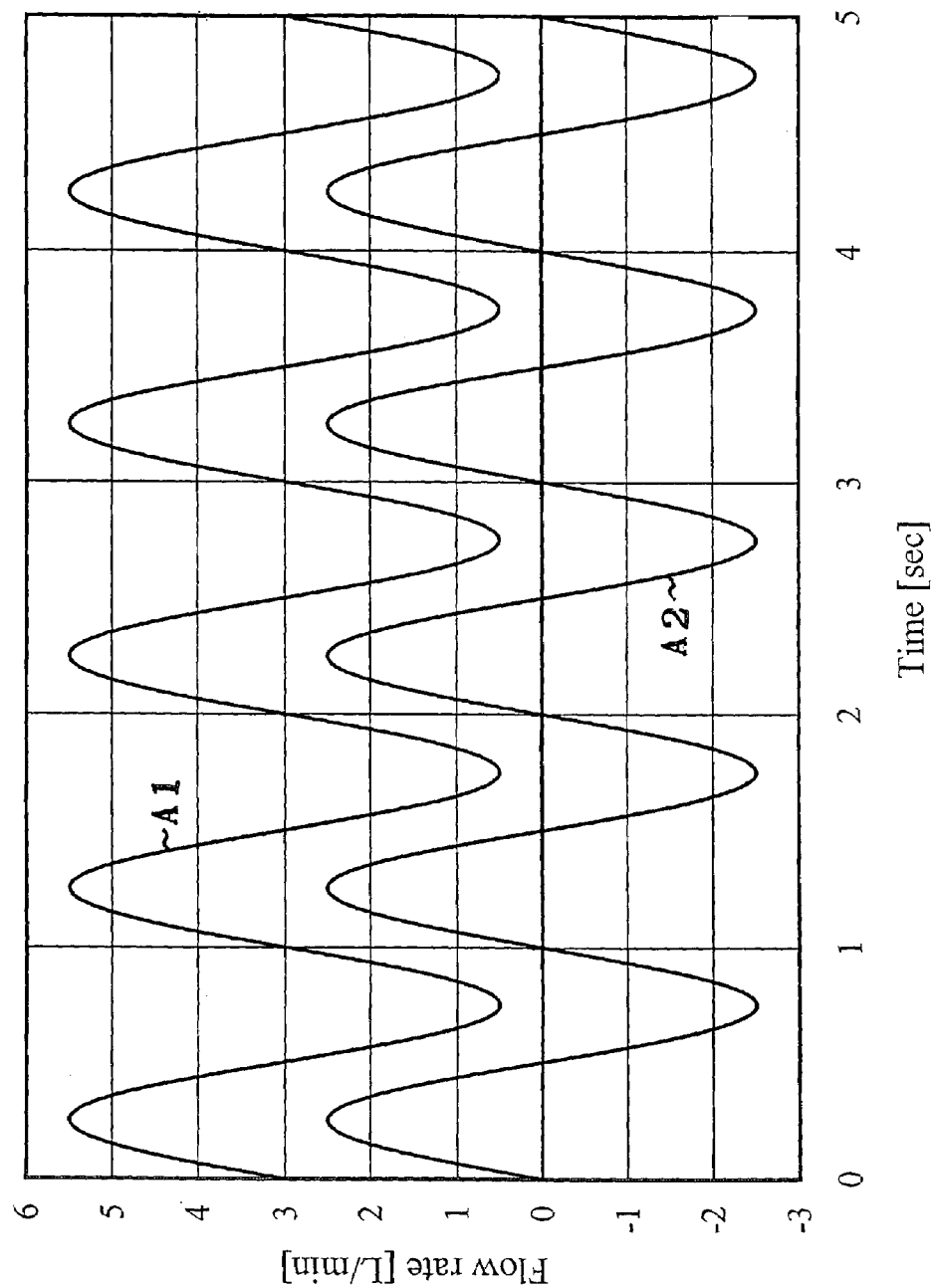
FIG. 11 is a graph showing the relationship between blood flow rate and time.

FIG. 11 is a graph showing the relationship between blood flow rate and time, in which A1 is the relationship between blood flow rate and time in the condition where backflow is absent, and A2 is the relationship between blood flow rate and time in the condition where a backflow is present. The flow rate varies in this manner due to the pulsation of a heart. Incidentally, in the figure, a modification into a sine wave condition is adopted for illustration.

Figure 12:
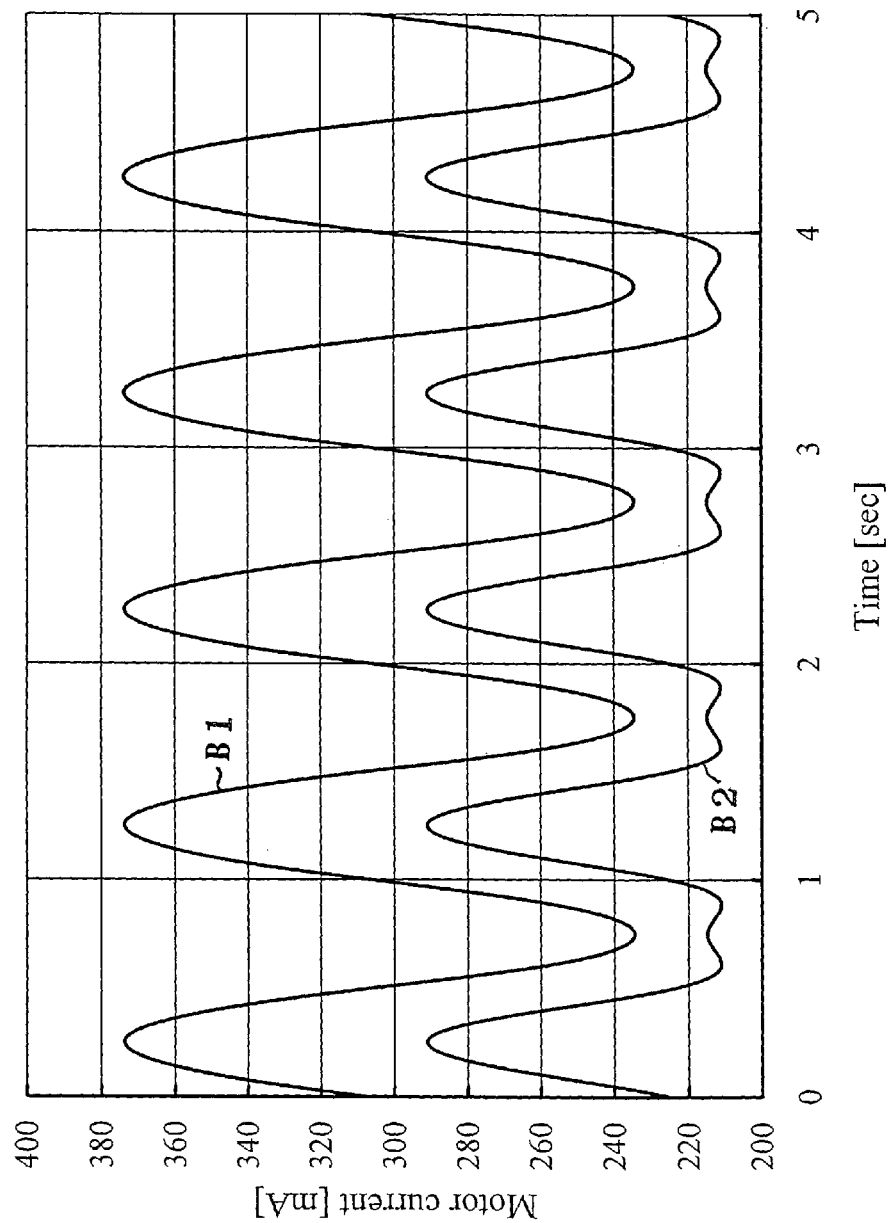
FIG. 12 is a graph showing the relationship between motor current and time.

FIG. 12 is a graph showing motor current value and time at a certain rotational speed (specifically, 1200 rpm), in which B1 is the relationship between motor current value and time in the condition where backflow is absent, and B2 is the relationship between motor current value and time in the condition where a backflow is present. The motor current value varies in this manner due to the pulsation of a heart.

Figure 6:
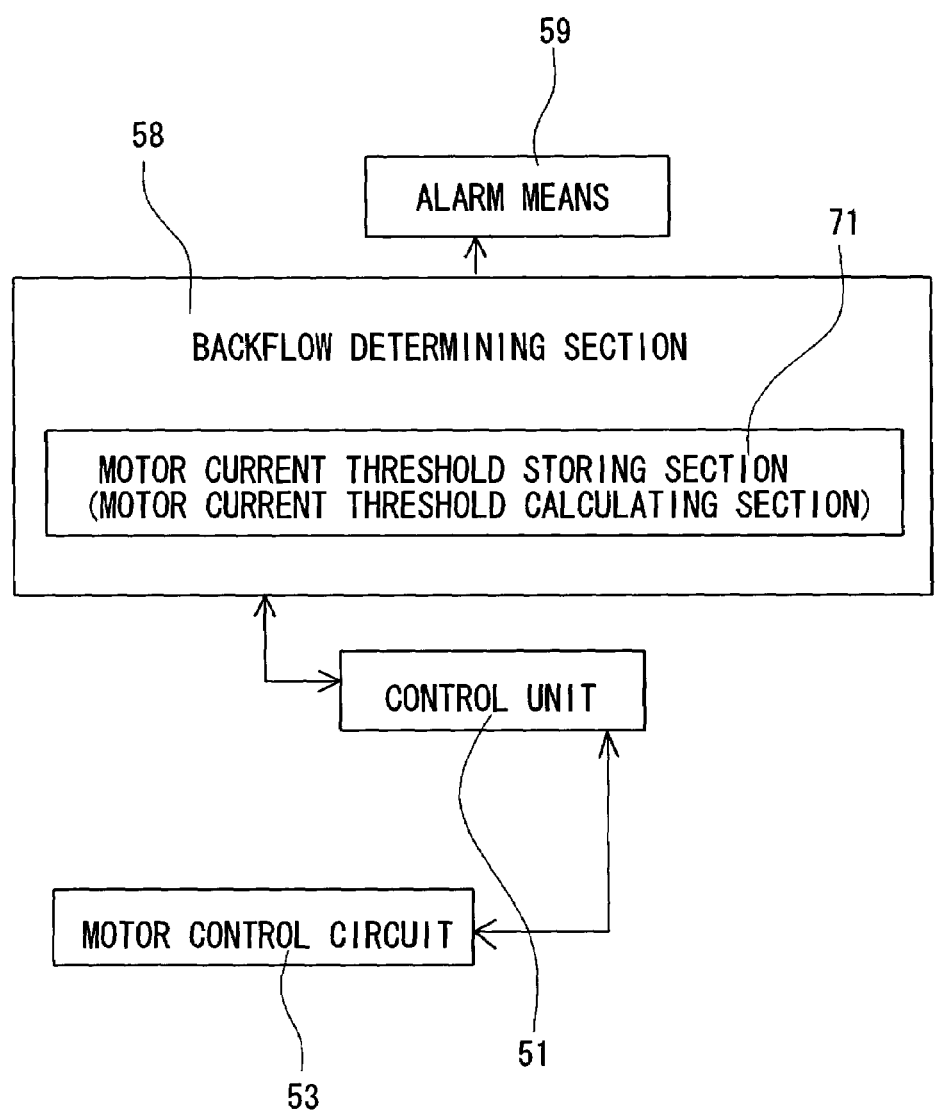
FIG. 6 is a block diagram for illustrating one embodiment of a backflow determining function in the blood pump system according to the present invention.

FIG. 6 is a block diagram for illustrating one embodiment of the backflow determining function.

The backflow determining function in this embodiment is to determine the generation of a backflow by use of a motor current threshold storing or calculating section 71 for storing or calculating a motor current threshold which varies according to the rotational speed of the rotor (impeller) 21, and the motor current value measured by the motor current measuring function and the motor current threshold.

This type of backflow determining function preferably comprises a motor current threshold storing or calculating function for storing or calculating a motor current threshold (in other words, motor current threshold storing section 71 or motor current threshold calculating section) which varies according to the rotational speed of a rotor (in this embodiment, an impeller or a motor), and a function of determining, when the period of time when the motor current value measured by the motor current measuring function is not more than the motor current threshold at the rotational speed has reached or exceeded a predetermined period of time, that a backflow is present.

To be more specific, the motor current threshold storing or calculating section 71 stores or calculates the motor current threshold which varies according to the rotational speed. Namely, a motor current threshold storing section for storing the motor current threshold at each rotational speed or a motor current calculating section for calculating the motor current threshold at each rotational speed is provided. Where the motor current threshold calculating section is provided, the calculating section stores a motor current threshold calculation expression, and calculates the motor current threshold by use of a motor rotational speed (impeller rotational speed) signal outputted from the control unit and inputted to the determining section. The motor current threshold in this embodiment is a low motor current value which cannot be taken under normal conditions (namely, in the condition where backflow is absent). To be more specific, in the case as shown in FIG. 12, the motor current threshold is, for example, 230 mA. Incidentally, the motor current threshold varies according to the motor rotational speed, i.e. the rotational speed of the rotor (in this embodiment, the impeller). Therefore, the backflow determining section comprises a function of storing or calculating the motor current threshold at each motor rotation speed, as described above.

The motor current threshold can be calculated, for example, by the following operation expression:

$$Vth = 230 + 0.2(N - 1200)$$

where N is the motor rotational speed.

Then, when the period of time when the measured motor current value is not more than the threshold has reached or exceeded a predetermined period of time, in this embodiment, it is determined that a backflow is present. The predetermined period of time is preferably 10% of the period of measurement. The period of measurement here is the period of time for which the motor current value is continuously picked up by motor current measurement for detection of backflow (Record Time).

In addition, the backflow generation determining function may be configured as follows.

Figure 7:
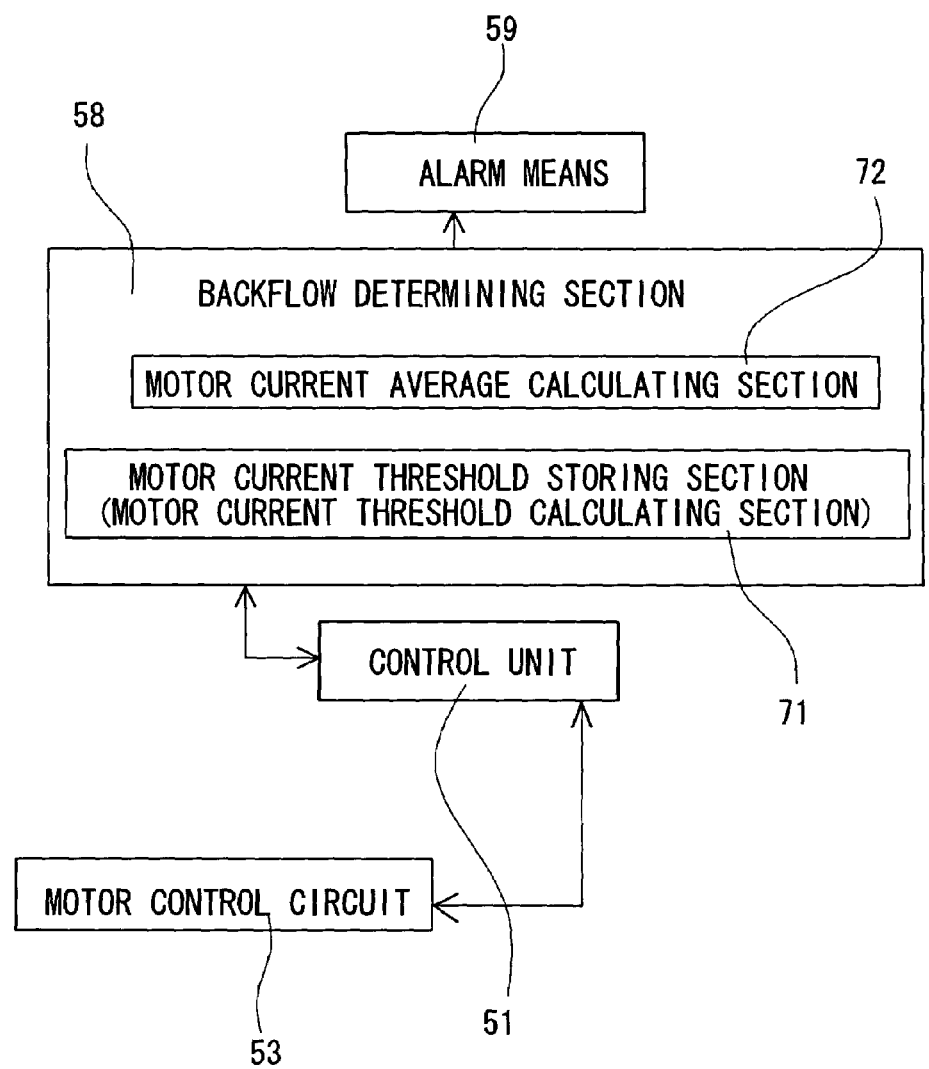
FIG. 7 is a block diagram for illustrating another embodiment of the backflow determining function in the blood pump system according to the present invention.

FIG. 7 is a block diagram for illustrating another embodiment of the backflow generation determining function.

The backflow detecting function 58 in this embodiment may comprise a motor current threshold storing or calculating function for storing or calculating a motor current threshold (in this embodiment, motor current threshold storing section 71 or motor current threshold calculating section) which varies according to the rotational speed of a rotor (in this embodiment, an impeller or a motor), a motor current average calculating function (in this embodiment, motor current average calculating section 72), and a function of determining, when the average over a predetermined period of time of the motor current value measured by a motor current measuring function is lowered to or below a motor current threshold or when the condition where the average is not more than the motor current threshold at the rotational speed has continued, that a backflow is present.

In this embodiment, also, the motor current threshold storing section and the motor current threshold calculating section are the same as the above-described. The calculation of the threshold can be performed by use of the above-mentioned operation expression.

In this embodiment, a backflow determining section 58 comprises a motor current average calculation function (motor current average calculation section 72) for calculating the average over a predetermined period of time of the motor current value measured by a motor current measuring function. The predetermined period of time is preferably 3 to 10 sec. When the average is lowered to or below the motor current threshold, it is determined that a backflow is present.

Besides, in place of the function of determining, when the motor current average is only once lowered to or below the motor current threshold, that a backflow is present, a function may be adopted which determines, when the condition where the motor current average is not more than the motor current threshold at the rotational speed has continued, that a backflow is present. The number of times of continuation varies depending on the average calculation period, and may be two or more. An appropriate number of times of continuation is considered to be 2 to 10 times.

Further, a function may be adopted which determines, when the condition where the motor current average is not more than the motor current threshold at the rotational speed has occurred intermittently, that a backflow is present. The number of times of occurrence may be two or more times. An appropriate number of times of occurrence is considered to be 2 to 10 times. Besides, the intermittent occurrence detection period is preferably about 15 to 30 sec.

In addition, the backflow generation determining function may be configured as follows.

Figure 8:
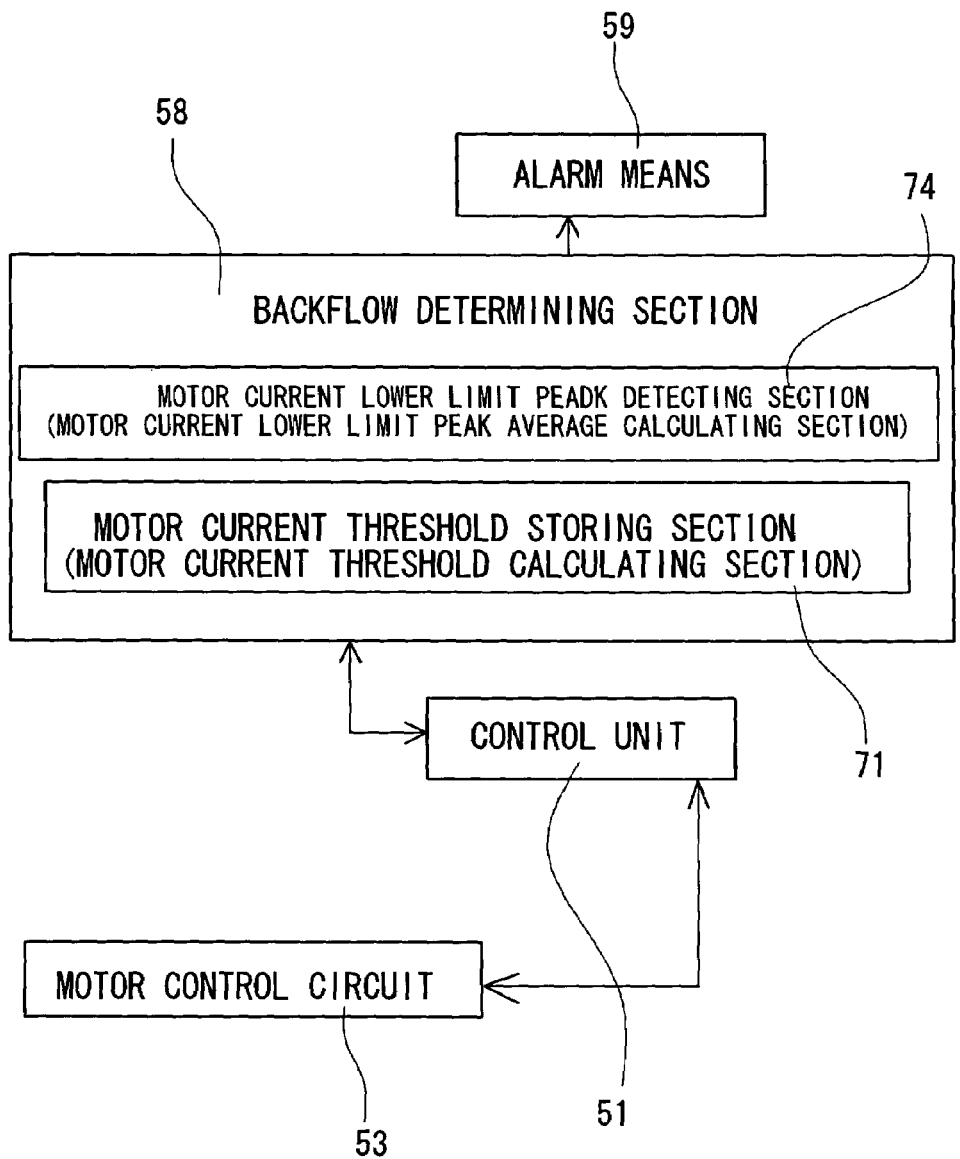
FIG. 8 is a block diagram for illustrating a further embodiment of the backflow determining function in the blood pump system according to the present invention.

FIG. 8 is a block diagram for illustrating a further embodiment of the backflow determining function.

The backflow detecting function 58 in this embodiment comprises a motor current threshold storing or calculating function for storing or calculating a motor current threshold (in this embodiment, motor current threshold storing section 71 or motor current threshold calculating section) which varies according to the rotational speed of a rotor (in this embodiment, an impeller or a motor), a function of detecting a sequential motor current lower limit peak value from a motor current value sequentially measured by a motor current measuring function, and a function of determining, when the motor current lower limit peak value is lowered to or below the motor current threshold at the rotational speed or when the condition where the motor current lower limit peak value is not more than the motor current threshold at the rotational speed has continued, that a backflow is present.

In this embodiment, also, the motor current threshold storing section and the motor current threshold calculating section are the same as the above-described. In addition, the above-mentioned operation expression may be used.

In this embodiment, a backflow determining section 58 comprises a motor current low limit peak value detecting section 74 for detecting the sequential motor current lower limit peak value from the motor current value measured by a motor current measuring function. When the lower peak value is lowered to or below the motor current threshold, it is determined that a backflow is present.

In addition, in place of the function of determining, when the motor current lower limit peak value is only once lowered to or below the motor current threshold, that a backflow is present, a function may be adopted which determines, when the condition where the motor current lower limit peak value is not more than the motor current threshold has continued, that a backflow is present. The number of times of continuation may be two or more. An appropriate number of times of continuation is considered to be 2 to 20 times. Besides, the continuation may not be in terms of the number of times but may be in terms of a predetermined period of time, which is preferably about 5 to 30 sec.

Besides, in this embodiment, a function may be adopted which determines, when the average over a predetermined period of time of the motor current lower limit peak value is lowered to or below the motor current threshold at the rotational speed or when the condition where the motor current lower limit peak value average is not more than the motor current threshold at the rotational speed has continued, that a backflow is present. The predetermined period of time for calculation of the average is preferably 5 to 10 sec. The number of times of continuation for determination of backflow may be two or more. An appropriate number of times of continuation is considered to be 2 to 4 times. In addition, the continuation may not be in terms of the number of times but may be in terms of a predetermined period of time, which is preferably about 10 to 30 sec.

Besides, the backflow generation determining function may be configured as follows.

Figure 9:
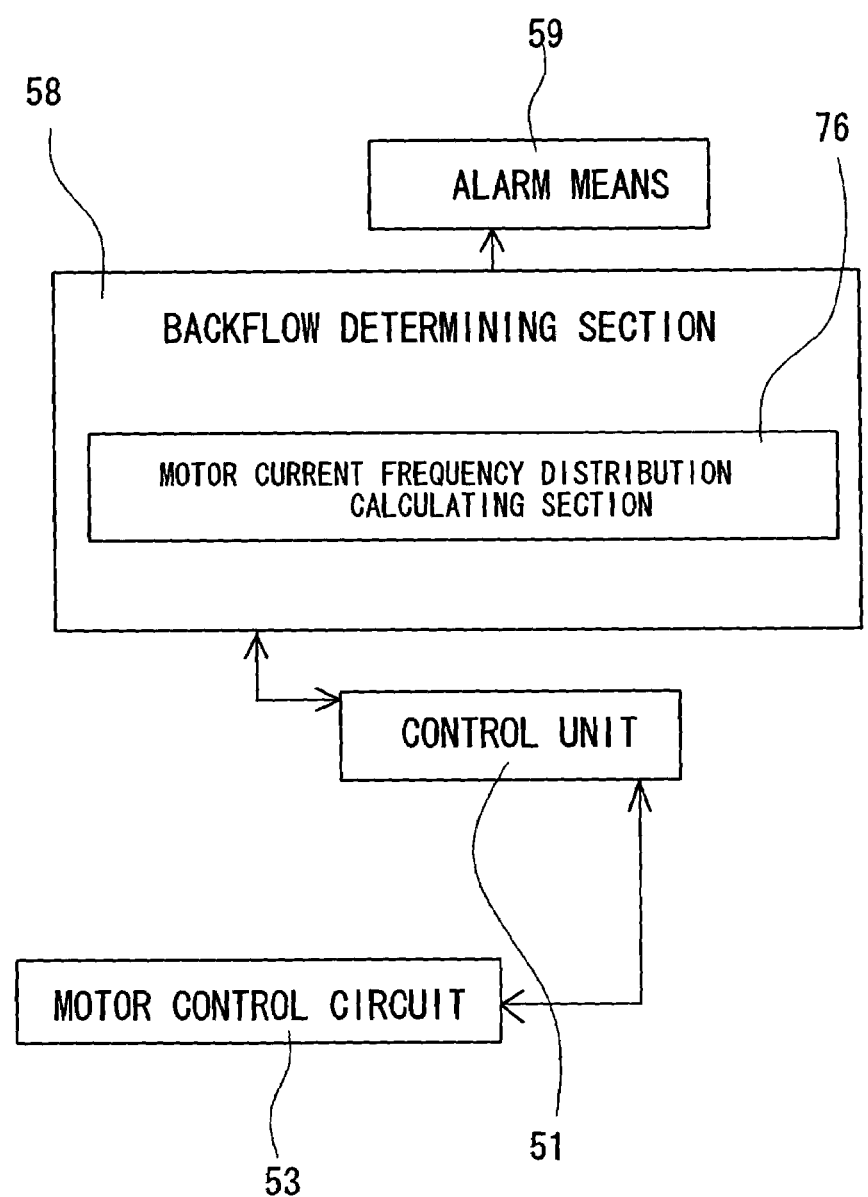
FIG. 9 is a block diagram for illustrating still another embodiment of the backflow determining function in the blood pump system according to the present invention.

FIG. 9 is a block diagram for illustrating still another embodiment of the backflow determining function.

The backflow detecting function in this embodiment comprises a motor current frequency distribution calculation function for calculating a frequency distribution by use of the motor current value in a predetermined period of time measured by a motor current measuring function, and a function of determining the generation of a backflow by use of the frequency distribution calculated by the motor current frequency distribution calculation function.

A backflow determining section 58 in this embodiment comprises the motor current frequency distribution calculation section 76. The motor current frequency distribution can be obtained, for example, from the continuously measured motor current value by use of outputs of a plurality of band pass filters using FFT (Fast Fourier Transform) and analog circuits, or the like means.

This type of backflow detecting function comprises, for example, a motor current frequency distribution calculation function for calculating a frequency distribution by use of the motor current value in a predetermined period of time measured by a motor current measuring function, and a function of determining, when the intensity of a secondary harmonic wave in the frequency distribution calculated by the motor current frequency calculation function is increased to or above a predetermined proportion of the intensity of a fundamental wave in the frequency distribution or when the condition where the intensity of the secondary harmonic wave in the frequency distribution calculated by the motor current frequency distribution calculation function is not less than a predetermined proportion of the intensity of the fundamental wave has continued, that a backflow is present.

Figure 13:
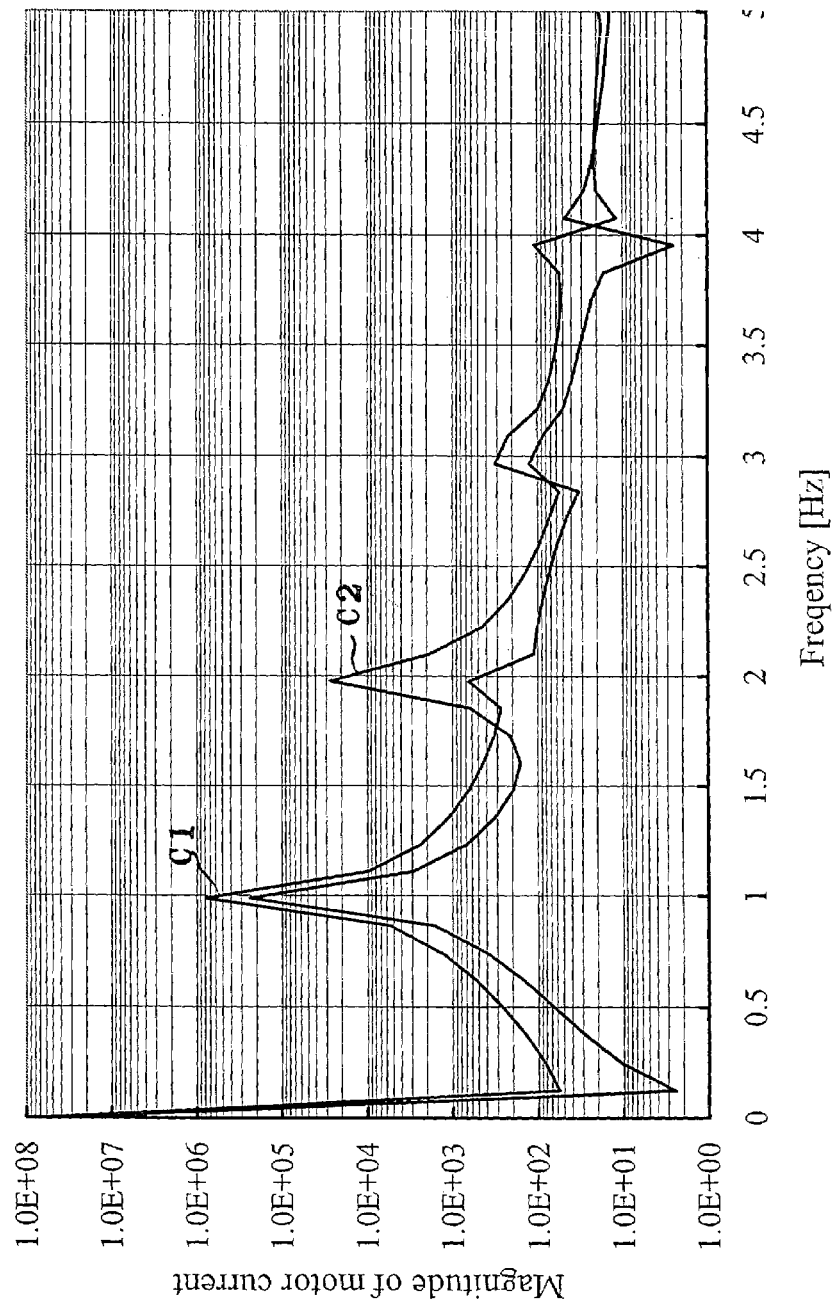
FIG. 13 is a graph showing motor current frequency distribution.

FIG. 13 is a graph showing a motor current frequency distribution, in which C1 is the motor current frequency distribution in the condition where backflow is absent, and C2 is the motor current frequency distribution in the condition where a backflow is present. Specifically, FIG. 13 shows one example of analytical results of motor current frequency in the case where blood flow rate varies in the form of a sine wave with a frequency of 1 Hz. Even in the flow rate waveform at 1 Hz, higher harmonics appear because the pump flow rate and the motor current are in a non-linear relationship. As shown in the figure, the magnitude of the secondary harmonic wave relative to the fundamental wave in the case where a backflow is present is much greater than that in the case where backflow is absent.

When the intensity of the secondary harmonic wave is increased to or above a predetermined proportion of the intensity of the fundamental wave, the backflow determining function in this embodiment determines that a backflow is present. The predetermined proportion is preferably 0.3% based on the fundamental wave. Namely, it is preferable to determine, when the intensity of the secondary harmonic wave is increased to or above 0.3% of the intensity of the fundamental wave, that a backflow is present.

In addition, a function may be adopted which determines, when the condition where the intensity of the secondary harmonic wave is not less than a predetermined proportion of the intensity of the fundamental wave has continued, that a backflow is present. The number of times of continuation for determination of backflow may be two or more times. An appropriate number of times of continuation is considered to be 2 to 4 times. Besides, the continuation may not be in terms of the number of times but may be in terms of a predetermined period of time, which is preferably about 10 to 100 sec.

Besides, the backflow generation determining function may be configured as follows.

Figure 10:
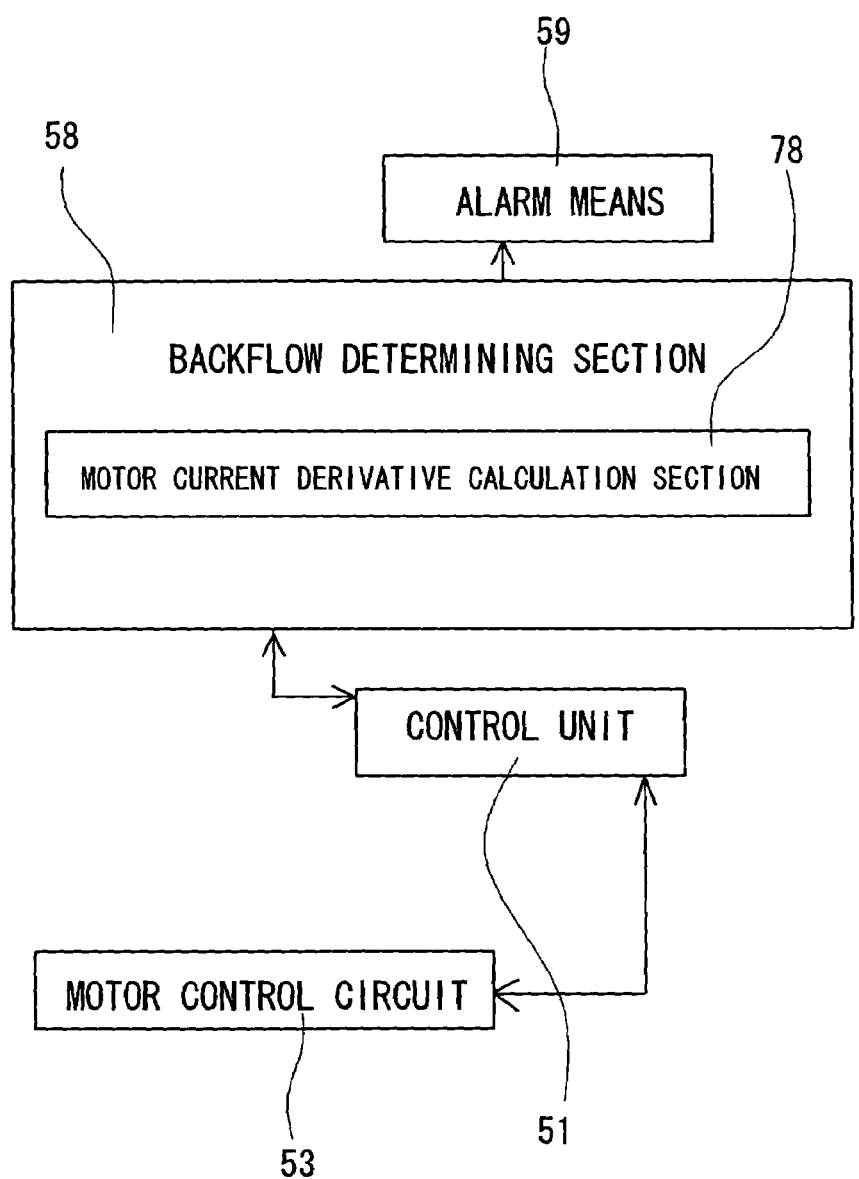
FIG. 10 is a block diagram for illustrating a still further embodiment of the backflow determining function in the blood pump system according to the present invention.

FIG. 10 is a block diagram for illustrating a still further embodiment of the backflow determining function.

The backflow determining function in this embodiment comprises a derivative (in other words, differential) calculation function for calculating a derivative (in other words, differential) by use of the motor current value sequentially measured by a motor current measuring function, and a function of determining the generation of a backflow by use of the derivative calculated by the motor current derivative calculation function.

A backflow determining section 58 in this embodiment comprises the motor current derivative calculation section 78 (in other words, the motor current differential calculation section). The motor current derivative (the motor current differential) is calculated by use of two adjacent current values of the motor current measured sequentially and continuously.

Figure 14:
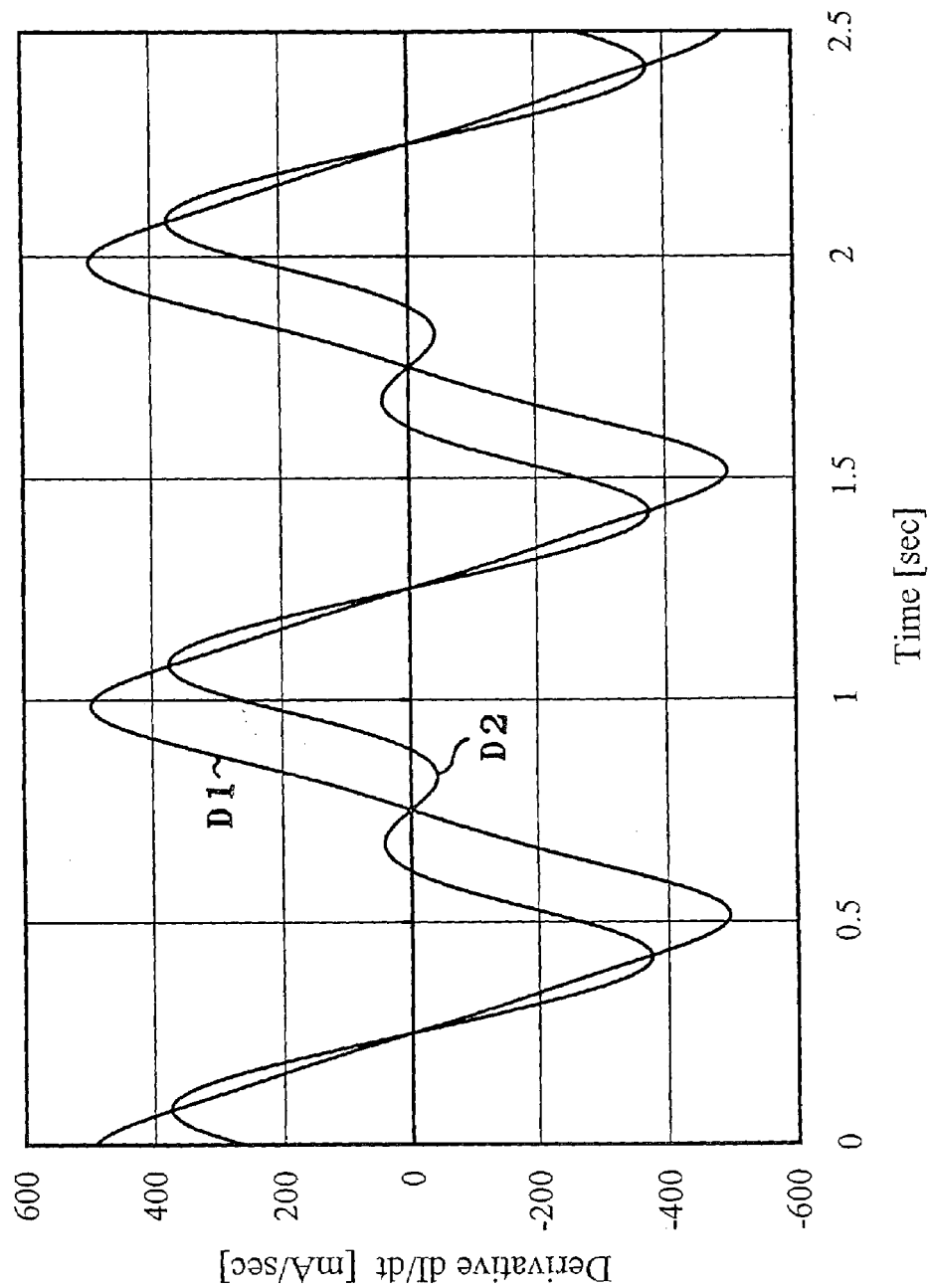
FIG. 14 is a graph showing the relationship between motor current derivative and time.

FIG. 14 is a graph showing the relationship between motor current derivative and time at a certain rotational speed (specifically, 1200 rpm), in which D1 is the relationship between motor current derivative and time in the condition where backflow is absent, and D2 is the relationship between motor current derivative and time in the condition where a backflow is present. As shown in the figure, different curves are obtained in the case where a backflow is present and in the case where backflow is absent.

The backflow detecting function in this embodiment comprises, for example, a motor current derivative calculation function for calculating a derivative by use of the motor current value sequentially measured by a motor current measuring function, and a function of determining, when the condition where the generation of zero points of the derivative calculated by the motor current derivative calculation function in a predetermined period of time is increased has continued, that a backflow is present. The backflow detecting function in this embodiment is to determine, when the frequency of generation of zero points of the derivative is increased, that a backflow is present.

As shown in FIG. 14, in the condition where backflow is absent, the derivative becomes zero twice between top peaks (in one period). On the other hand, in the condition where a backflow is present, the derivative becomes zero four times between the top peaks (in one period), as shown in FIG. 14; namely, the frequency of generation of zero points is increased. Therefore, generation of a backflow can be determined by detecting the increase in the frequency of generation of zero points of the derivative.

A specific method of determining, when the condition where the generation of zero points of the derivative is increased has continued, that a backflow is present is, for example, a method of determining, when the number of times of the generation of zero point in a predetermined period of time reaches or exceeds a predetermined number of times, that a backflow is present. The predetermined period of time is preferably the period between the top peaks (one period), and may be 2 to 4 periods. The predetermined number of times for determination of backflow is preferably twice. In addition, the number of times of continuation for determination of backflow may be two or more times. An appropriate number of times of continuation is considered to be 2 to 20 times. Besides, the continuation may not be in terms of the number of times but may be in terms of a predetermined period of time, which is preferably about 5 to 30 sec.

In addition, this type of backflow detecting function may comprise, for example, a motor current derivative calculation function for calculating a derivative by use of the motor current value sequentially measured by a motor current measuring function, and a function of determining, when the period of generation of zero points of the derivative calculated by the motor current derivative calculation function in a predetermined period of time has become greater than the frequency between motor current upper limit peaks higher than the average of the motor current or when this condition has continued, that a backflow is present. The backflow detecting function in this embodiment is of the type of determining, when the frequency of generation of zero points of the derivative has become higher than the top peak frequency, that a backflow is present.

As shown in FIG. 14, in the condition where backflow is absent, the derivative becomes zero twice between top peaks (in one period). In the condition where backflow is absent, as indicated by D1 in FIG. 14, the top peak period and the zero point generation period are staggered by ½ period, but the lengths of time of one period are substantially equal and the frequencies are equal. On the other hand, in the case where a backflow is present, as indicated by D2 in FIG. 14, the top peak period is substantially the same as in the case where backflow is absent, but the zero point generation period is irregular and the frequency thereof is about 2 times. Therefore, generation of a backflow can be determined by detecting that the zero point generation frequency has become greater than the frequency between the motor current upper limit peaks higher than the average of motor current.

Besides, the backflow generation determination may reside in a function of determining, when the condition where the zero point generation frequency is greater than the frequency between the motor current upper limit peaks higher than the average of motor current has continued, that a backflow is present. A specific example of the method of determining, when the above-mentioned condition has continued, that a backflow is present is a method of making such a determination when it is detected that the condition has occurred successively a predetermined number of times. The number of times of continuation for determination of backflow may be two or more times. An appropriate number of times of continuation is considered to be 2 to 20 times. In addition, the continuation may not be in terms of the number of times but may be in terms of a predetermined period of time, which is preferably about 5 to 30 sec.

Besides, this type of backflow detecting function may comprise, for example, a motor current derivative calculation function for calculating a derivative by use of the motor current value sequentially measured by a motor current measuring function, and a function of determining, when the generation of zero points of the derivative calculated by the motor current derivative calculation function in a predetermined period of time appears repeatedly in shorter periods and longer periods or when this condition has continued, that a backflow is present. The backflow generation determining function in this embodiment is of the type of determining, when the zero point period of the derivative consists of repetition of shorter periods and longer periods, that a backflow is present.

As shown in FIG. 14, in the condition where backflow is absent, the period of zero points of the derivative is substantially constant, as indicated by D1 in FIG. 14. On the other hand, in the condition where a backflow is present, two successive longer periods and two successive shorter periods appear repeatedly, as indicated by D2 in FIG. 14. By detecting this condition, it is possible to determine that a backflow is present.

Thus, the backflow determining function in this embodiment comprises the above-mentioned derivative calculation function, and a function of calculating the zero point generation time interval of the derivative calculated by the derivative calculation function. It is determined, when a longer time interval and a sufficiently shorter time interval are detected in the time intervals calculated by the zero point generation time interval calculating function, that a backflow is present. The shorter time interval is preferably not more than ⅓ times the longer timer interval.

In addition, the backflow generation determination may reside in a function of determining, when a shorter period and a longer period appear repeatedly in the zero point period of the above-mentioned derivative, in other words, when the condition where a shorter time interval appears in the above-mentioned zero point generation time intervals has continued, that a backflow is present. A specific example of the method of determining, when the above-mentioned condition has continued, that a backflow is present is a method of making such a determination when it is detected that the condition has occurred successively a predetermined number of times. The number of times of continuation for determination of backflow may be two or more times. An appropriate number of times of continuation is 2 to 20 times. Besides, the continuation may not be in terms of the number of times but may be in terms of a predetermined period of time, which is preferably about 5 to 30 sec.

In addition, this type of backflow detecting function may comprise, for example, a motor current derivative calculation function for calculating a derivative by use of the motor current value sequentially measured by a motor current measuring function, a derivative threshold storing section (in other words, a differential threshold storing section) for storing a derivative threshold (in other words, a differential threshold) for determination, and a function of determining, when the derivative calculated by the motor current derivative calculation function has come within a derivative threshold (in other words, a differential threshold) under a predetermined condition or when the condition where the derivative is within the derivative threshold (in other words, the differential threshold) under a predetermined condition has occurred repeatedly, that a backflow is present. The backflow generation determining function in this embodiment is of the type of determining, when the derivative is in the vicinity of zero for a long time, that a backflow is present.

As shown in FIG. 14, in the condition where backflow is absent, the derivative continuously varies largely in the vicinity of zero. Therefore, the period of time for which the derivative is in the vicinity of zero is short. On the other hand, in the condition where a backflow is present, as indicated by D2 in FIG. 14, the derivative has two small peaks in the vicinity of zero and there is generated the condition where the derivative is in the vicinity of zero for a long time. Therefore, by detecting this condition, it is possible to determine that a backflow is present.

Thus, the backflow determining function in this embodiment comprises the above-mentioned derivative calculation function, and the derivative threshold storing function or the derivative threshold calculation function. When it is detected that the derivative sequentially calculated has come within the above-mentioned derivative threshold under a predetermined condition, it is determined that a backflow is present. The derivative threshold is preferably not more than 100 mA/sec. The predetermined condition for determination is preferably a condition where not less than 15% of the derivative in a predetermined period of time has been in the above-mentioned condition.

Besides, the backflow generation determination may be to determine, when the condition where the derivative is within the derivative threshold for the predetermined period of time has occurred repeatedly, that a backflow is present. A specific example of the method of determining, when the above-mentioned condition has continued, that a backflow is present is a method of making such a determination when it is detected that the condition has occurred successively a predetermined number of times. The number of times of continuation for determination of backflow may be two or more times. An appropriate number of times of continuation is considered to be 2 to 20 times. In addition, the continuation may not be in terms of the number of times but may be in terms of a predetermined period of time, which is preferably about 5 to 30 sec.

When a backflow is detected, the control unit 51 operates the alarm means 59 to inform the user of the generation of the backflow. Further, the control unit 51 preferably comprise a function of increasing the rotational speed of the motor when the backflow has been detected.

Figure 15:
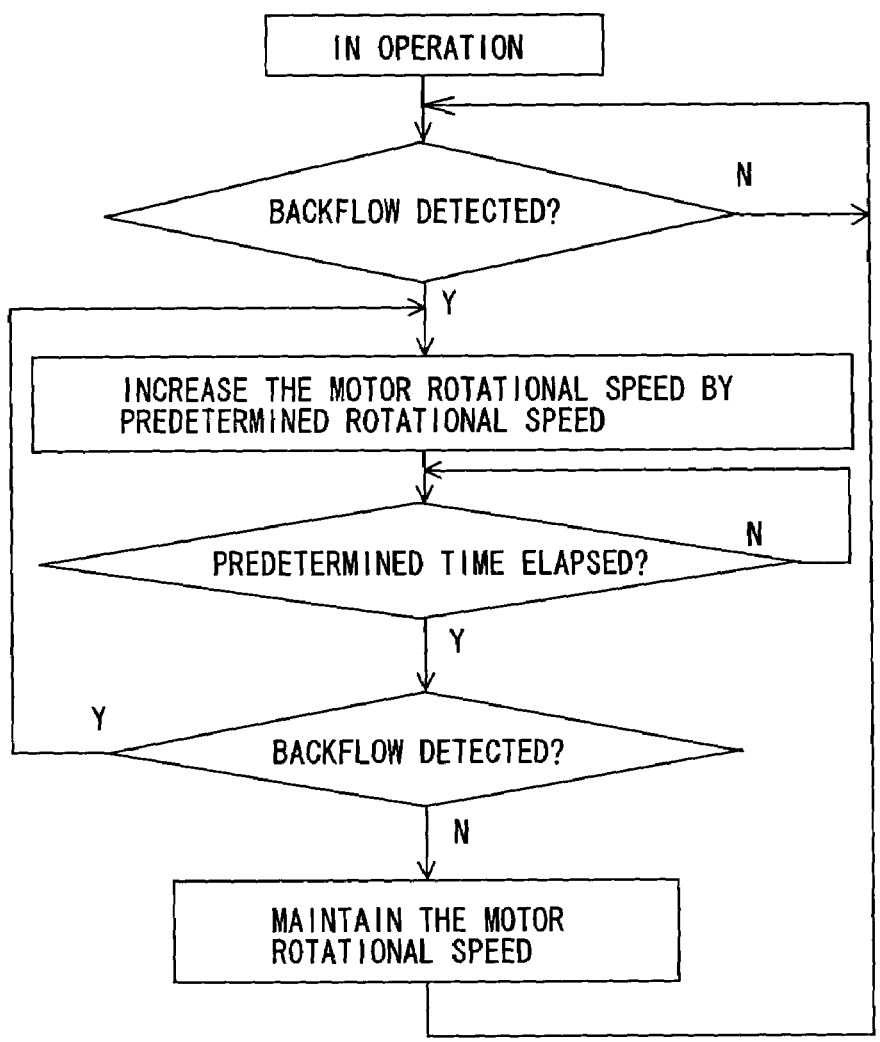
FIG. 15 is a flow chart for illustrating a control mechanism in the blood pump system according to the present invention.

Specifically, it is desirable to perform a control as represented by the flow chart shown in FIG. 15.

In this embodiment, the control unit 51 comprises a function of increasing the motor rotational speed by a stored predetermined rotational speed when a backflow has been detected, a function for maintaining the motor rotational speed at the rotational speed when the backflow is cancelled by the operation of the above function, and a function of again increasing the motor rotational speed when the backflow has not been cancelled by the increase of the motor rotational speed.

To be more specific, as shown in FIG. 15, detection of backflow is normally conducted during operation of the blood pump, and when generation of a backflow is detected, the control unit 51 increases the motor rotational speed by a predetermined rotational speed. The predetermined rotational speed (increment of rotational speed) is preferably 10 to 50 rpm. The increase in the motor rotational speed increases the flow rate, thereby canceling the generation of backflow. After a predetermined lapse of time from the increase of the motor rotational speed, detection of backflow is again conducted. The predetermined lapse of time here is preferably about 60 to 180 sec. When backflow is not detected, or when the generation of backflow is cancelled, the motor rotational speed is maintained, and normal backflow detection is again continued. When a backflow is detected even upon the determination after the predetermined lapse of time from the increase of the motor rotational speed, the motor rotational speed is again increased. Thereafter, the same procedure as above is carried out.

Figure 16:
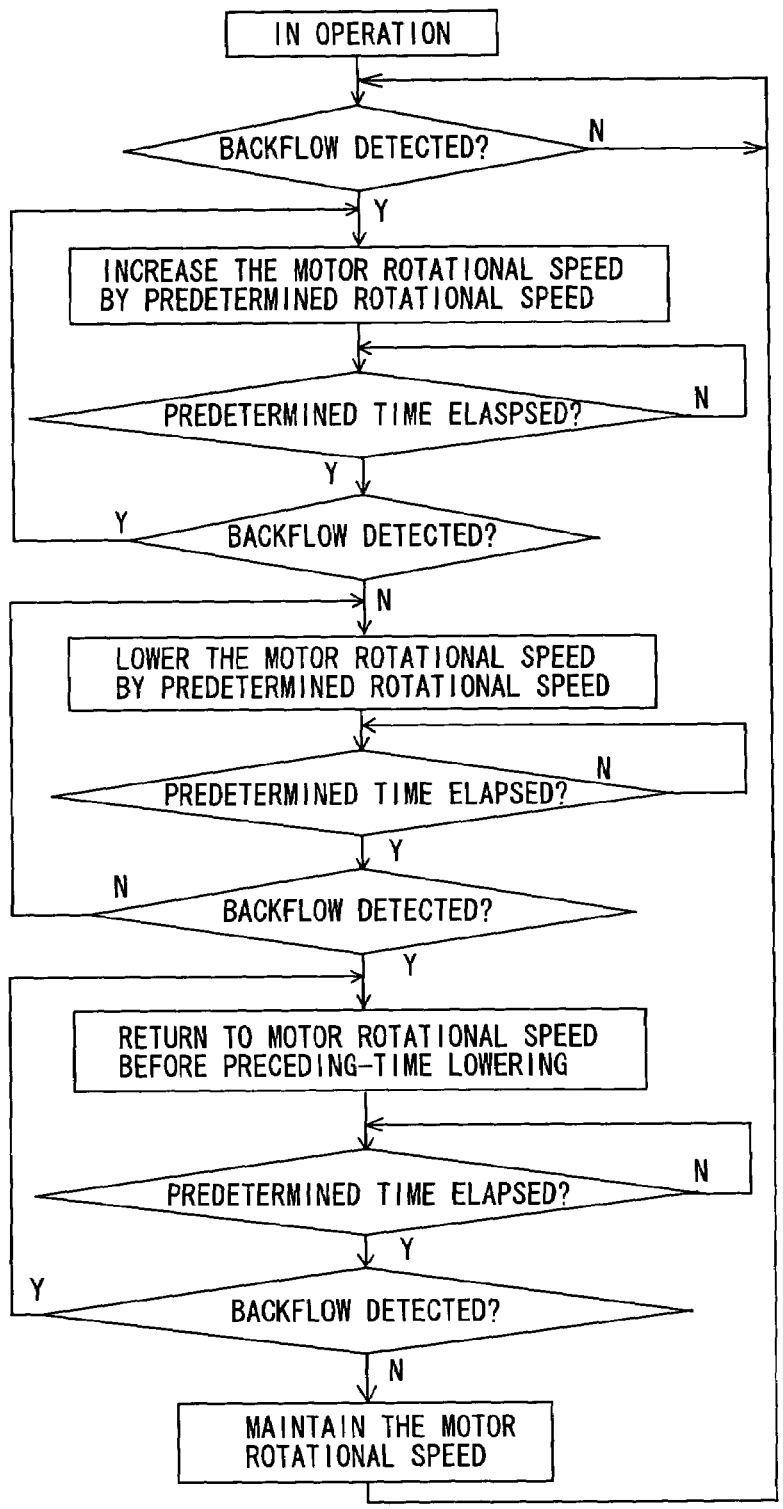
FIG. 16 is a flow chart for illustrating the control mechanism in the blood pump system according to the present invention.

In addition, it is more desirable to perform a control as represented by the flow chart shown in FIG. 16.

In this embodiment, the control unit 51 comprises a function of increasing the motor rotational speed by a stored predetermined rotational speed when a backflow is detected, a function of lowering the motor rotational speed by a predetermined rotational speed (second predetermined rotational speed) lower than the predetermined rotational speed for increase (first predetermined rotational speed) when the backflow is canceled by the operation of the above function, a function of again lowering the motor rotational speed by a predetermined rotational speed (for example, the second predetermined rotational speed) lower than the predetermined rotational speed for increase (first predetermined rotational speed) when backflow is not detected after the lowering of the rotational speed, a function of returning the motor rotation speed to the preceding-time motor rotational speed (in other words, increasing the motor rotational speed by the second predetermined rotational speed or a third predetermined rotational speed) when a backflow is detected after the lowering of the motor rotational speed, and a function of again increasing the motor rotation speed when the backflow is not canceled even by the increase of the motor rotational speed by the predetermined rotational speed (first predetermined rotational speed).

This configuration ensures that a backflow generation condition can be dissolved early, and the motor can be rotated at a rotational speed close to the set rotational speed (the motor rotational speed before the increase of the motor rotational speed) and in such a condition where a backflow is not easily generated.

Specifically, as shown in FIG. 16, backflow detection is normally conducted during operation of the blood pump, and, upon detection of generation of a backflow, the control unit 51 increases the motor rotational speed by a predetermined rotational speed (first predetermined rotational speed). The predetermined rotational speed (first predetermined rotational speed) is preferably 10 to 50 rpm. The increase in the motor rotational speed increases the flow rate, thereby canceling the generation of the backflow. Then, after a predetermined lapse of time from the increase of the motor rotational speed, backflow detection is again conducted. The predetermined lapse of time here is preferably about 60 to 180 sec. When backflow is not detected, or when the generation of backflow has been canceled, the motor rotational speed is lowered by a predetermined rotational speed (second predetermined rotational speed). The second predetermined rotational speed is preferably 5 to 10 rpm. Besides, the second predetermined rotational speed is preferably $1/10$ to $1/2$ times the first predetermined rotational speed. Further, after a predetermined lapse of time from the lowering of the motor rotational speed, backflow detection is again conducted. The predetermined lapse of time here is preferably 60 to 180 sec. When backflow is not detected, the motor rotational speed is again lowered by the predetermined rotational speed (second predetermined rotational speed). This operation is repeated until a backflow is detected. When the backflow is detected, the motor rotational speed is returned to the preceding-time motor rotational speed, in other words, the motor rotational speed is increased by the second predetermined rotational speed. After a predetermined lapse of time from the returning (increasing) of the motor rotational speed, backflow detection is again conducted. When backflow is not detected, the current motor rotational speed is maintained, and normal backflow detection is again continued. On the other hand, when a backflow is detected even upon the determination after the predetermined lapse of time from the increasing of the motor rotational speed, the motor rotational speed is again returned to the preceding-time motor rotational speed, and this operation is repeated until detection of no backflow is realized. Then, when detection of no backflow is realized, the current motor rotational speed is maintained, and normal backflow detection is again continued.

In addition, when the backflow is not canceled even by the increase of the motor rotational speed by the predetermined rotational speed (first predetermined rotational speed), the motor rotational speed is again increased by the predetermined rotational speed. This increase of the rotational speed is repeated until detection of no backflow is realized. After detection of no backflow is realized, the above-mentioned lowering of the motor rotational speed is conducted.

Figure 17:
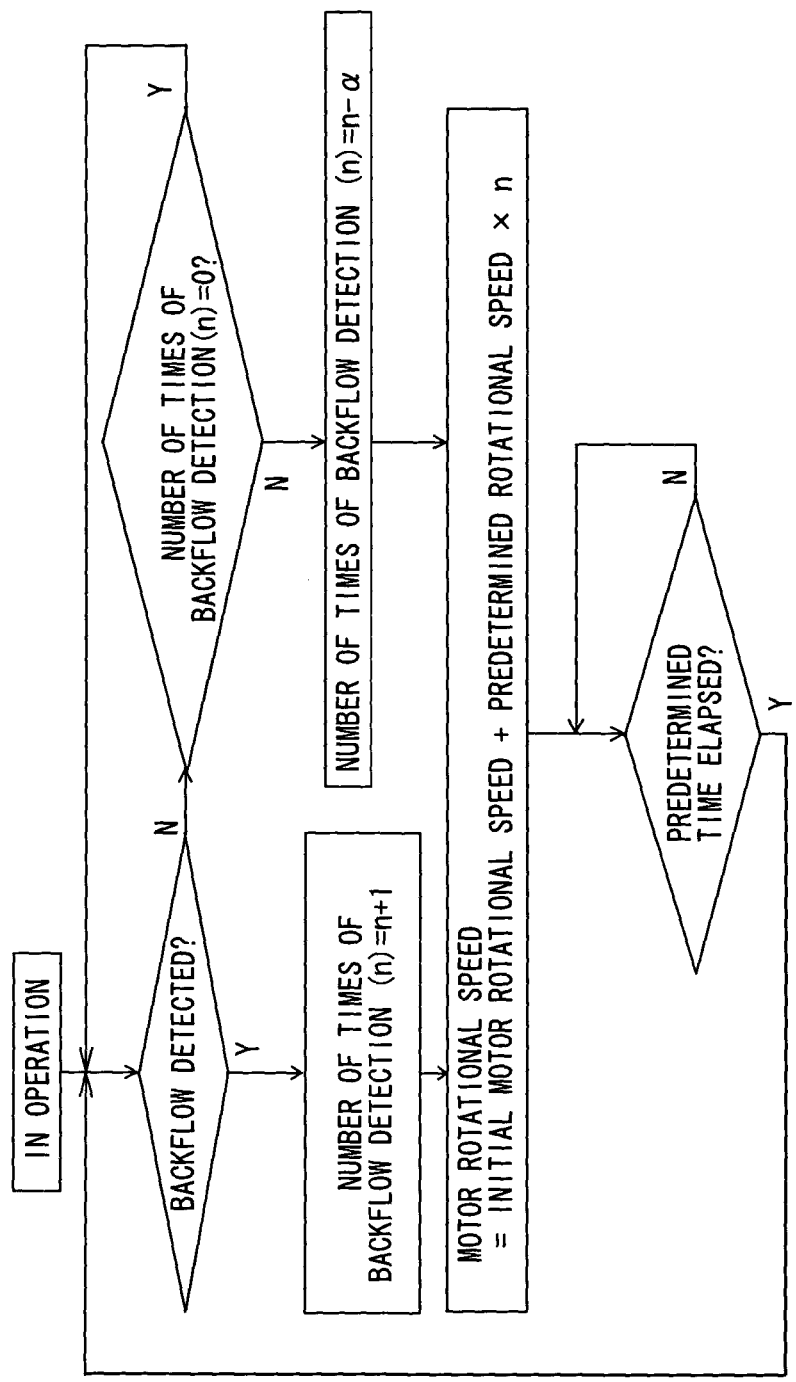
FIG. 17 is a flow chart for illustrating the control mechanism in the blood pump system according to the present invention.

Besides, it is also preferable to perform a control as represented by the flow chart shown in FIG. 17.

In this embodiment, the control unit 51 comprises a function of increasing the motor rotational speed by a stored predetermined rotational speed when a backflow is detected, a function of lowering the motor rotational speed by a predetermined rotational speed (second predetermined rotational speed) lower than the predetermined rotational speed for increase (first predetermined rotational speed) when the backflow is canceled by the operation of the above function, a function of again lowering the motor rotational speed by a predetermined rotational speed (for example, the second predetermined rotational speed) lower than the predetermined rotational speed for increase (first predetermined rotational speed) when backflow is not detected after the lowering of the motor rotational speed, and a function of lowering the motor rotational speed to an initial motor rotational speed when backflow is not detected after the lowering of the motor rotational speed.

This configuration ensures that a backflow generation condition can be canceled early, and a return to the set rotational speed (the motor rotational speed before the increase thereof) can be contrived.

Specifically, as shown in FIG. 17, backflow detection is normally conducted during operation of the blood pump, and, upon detection of generation of a backflow, the control unit 51 increases the motor rotational speed by a predetermined rotational speed (first predetermined rotational speed). The predetermined rotational speed (first predetermined rotational speed) is preferably 10 to 50 rpm. The increase in the motor rotational speed increases the flow rate, thereby canceling the generation of the backflow. After a predetermined lapse of time from the increase of the motor rotational speed, backflow detection is again conducted. The predetermined lapse of time here is preferably about 60 to 180 sec. Then, when a backflow is detected, the increase of the motor rotational speed is repeated until detection of no backflow is realized. Incidentally, the control unit 51 in this embodiment comprises a counter for storing the number of times of backflow detection (n). When a backflow is detected, an calculation of $n=n+1$ is performed to update n.

As shown in FIG. 17, the motor rotational speed is changed to a value which is calculated by the following expression:

Motor rotational speed=Initial motor rotational speed (Set motor rotational speed)+Predetermined rotational speed (First predetermined rotational speed)×$n$.

Namely, the motor rotational speed is increased by the predetermined rotational speed each time a backflow is detected.

Then, when n is not zero, in other words, when a backflow has precedingly been detected and detection of no backflow is realized by the increase of the rotational speed, that is, when the generation of backflow is canceled, the motor rotational speed is lowered by a predetermined rotational speed (second predetermined rotational speed). The second predetermined rotational speed is preferably ⅒ to ½ times the first predetermined rotational speed. Specifically, the control unit 51 in this embodiment comprises a counter for storing the number of times of backflow detection (n). When the stored n value is not zero, the control unit 51 in this embodiment performs an calculation of $n=n-\alpha$ to update n. The value of $\alpha$ is preferably ⅒ to ½. Then, by use of the above-mentioned motor rotational speed operation expression, the control unit 51 calculates a new motor rotational speed, and the motor rotational speed is changed. Thereafter, the motor rotational speed lowering function is continuously conducted until the condition of $n=0$ is reached, or until a backflow is again detected.

The blood pump system according to the present invention comprises a housing having an inlet port and an outlet port, a rotor rotated in the housing for pumping blood, and a motor for rotating the rotor, the blood pump system comprising a motor current measuring function, and a backflow detecting function for detecting a backflow of the blood by use of a motor current value continuously measured by the motor current measuring function. Therefore, the blood pump system of the present invention can detect a backflow without provision of a flow meter.

In addition, where the blood pump system comprises alarm means operated when it is determined by the backflow detecting function that a backflow is present, it is possible to inform the user of the generation of backflow detected.

Further, where the blood pump system comprises a rotational speed control function for increasing the rotational speed of the above-mentioned rotor when it is determined by the backflow detecting function that a backflow is present, it is possible to improve the backflow generation condition.

The present invention is not limited to the details of the above described preferred embodiments. The scope of the invention is defined by the appended claims and all changes and modifications as fall within the equivalence of the scope of the claims are therefore to be embraced by the invention.

What is claimed is:
1. A blood pump system which comprises:
a housing having an inlet port and an outlet port;
a rotor rotated in said housing for pumping blood;
a motor for rotating said rotor;
motor current measuring means for measuring motor current;
backflow detecting means for detecting a backflow of blood by use of the motor current value continuously measured by said motor current measuring means; and wherein said backflow detecting means comprises motor current threshold storing or calculating means for storing or calculating a motor current threshold varying according to a rotational speed of said rotor, and a backflow generation determining means for determining, when a period of time when said motor current value measured by said motor current measuring means is not more than said motor current threshold at the rotational speed has reached or exceeded a predetermined period of time, that a backflow is present.

2. A blood pump system as set forth in claim 1, comprising no direct flow rate detecting means.

3. A blood pump system as set forth in claim 1, comprising alarm means for producing an alarm which is operated when it is determined by said backflow detecting means that a backflow is present.

4. A blood pump system as set forth in claim 1, comprising a rotational speed control means for increasing the rotational speed of said rotor when it is determined by said backflow detecting means that a backflow is present.

5. A blood pump system as set forth in claim 1, wherein said rotor is an impeller for pumping blood by a centrifugal force upon rotation thereof.

6. A blood pump system as set forth in claim 1, comprising said housing having said inlet port and said outlet port, a centrifugal pump section having an impeller comprising a magnetic member therein and being rotated in said housing so as to pump blood by a centrifugal force upon rotation thereof the rotor comprising a magnet for attracting said magnetic member of said impeller of said centrifugal pump section, an impeller rotational torque generating section comprising the motor for rotating said rotor, and an impeller position control section comprising an electromagnet, wherein said impeller is rotated in said housing without any contact.

7. A blood pump system which comprises:
a housing having an inlet port and an outlet port;
a rotor rotated in said housing for pumping blood;
a motor for rotating said rotor;
motor current measuring means for measuring motor current;
backflow detecting means for detecting a backflow of blood by use of the motor current value continuously measured by said motor current measuring means; and
wherein said backflow detecting means comprises a motor current threshold storing or calculating means for storing or calculating a motor current threshold varying according to a rotational speed of said rotor, and a backflow generation determining means for determining, when an average over a predetermined period of time of said motor current value measured by said motor current measuring means has been lowered to or below said motor current threshold or when a condition where said average is not more than said motor current threshold at the rotational speed has been generated continuously or intermittently, that a backflow is present.

8. A blood pump system which comprises:
a housing having an inlet port and an outlet port;
a rotor rotated in said housing for pumping blood;
a motor for rotating said rotor;
motor current measuring means for measuring motor current;
backflow detecting means for detecting a backflow of blood by use of a motor current value continuously measured by said motor current measuring means; and
wherein said backflow generation detecting means comprises motor current threshold storing or calculating means for storing or calculating a motor current threshold varying according to a rotational speed of said rotor, and a backflow generation determining means for detecting a sequential motor current lower limit peak value from said motor current value sequentially measured by said motor current measuring means and for determining, when said motor current lower limit peak value has been lowered to or below said motor current threshold at the rotational speed or when the condition where said motor current lower limit peak value is not more than said motor current threshold at the rotational speed has continued, that a backflow is present.

9. A blood pump system which comprises:
a housing having an inlet port and an outlet port;
a rotor rotated in said housing for pumping blood;
a motor for rotating said rotor;
motor current measuring means for measuring motor current;
backflow detecting means for detecting a backflow of blood by use of a motor current value continuously measured by said motor current measuring means; and
wherein said backflow detecting means comprises a motor current threshold storing or calculating means for storing or calculating a motor current threshold varying according to a rotational speed of said rotor, and a backflow generation determining means for detecting a sequential motor current lower limit peak value from said motor current sequentially measured by said motor current measuring means and for determining, when an average over a predetermined period of said motor current lower limit peak value has been lowered to or below said motor current threshold at said rotational speed or when the condition where said average is not more than said motor current threshold at said rotational speed has continued, that a backflow is present.

10. A blood pump system which comprises:
a housing having an inlet port and an outlet port;
a rotor rotated in said housing for pumping blood;
a motor for rotating said rotor;
motor current measuring means for measuring motor current;
backflow detecting means for detecting a backflow of blood by use of a motor current value continuously measured by said motor current measuring means; and
wherein said backflow detecting means comprises a motor current derivative calculation means for calculating a derivative by use of the motor current value sequentially measured by said motor current measuring means, and a backflow generation determining means for determining generation of a backflow by use of said derivative calculated by said motor current derivative calculation means.

11. A blood pump system which comprises:
a housing having an inlet portion and an outlet port;
a rotor rotated in said housing for pumping blood;
a motor for rotating said rotor;
motor current measuring means for measuring motor current;
backflow detecting means for detecting a backflow of blood by use of a motor current value continuously measured by said motor current measuring means; and
wherein said backflow detecting means comprises a motor current derivative calculation means for calculating a derivative by use of the motor current value sequentially measured by said motor current measuring means, and a backflow generation determining means for determining when a condition where the generation of zero points of the derivative calculated by said motor current derivative calculation means in a predetermined period of time is increased has continued, that a backflow is present.

12. A blood pump system which comprises:
a housing having an inlet port and an outlet port;
a rotor rotated in said housing for pumping blood;
a motor for rotating said rotor;
motor current measuring means for measuring motor current;
backflow detecting means for detecting a backflow of blood by use of a motor current value continuously measured by said motor current measuring means; and
wherein said backflow detecting means comprises a motor current derivative calculation means for calculating a derivative by use of the motor current value sequentially measured by said motor current measuring means, and a backflow generation determining means for determining, when a period of generation of zero points of said derivative calculated by said motor current derivative calculating means in a predetermined period of time has become greater than a frequency between motor current upper limit peaks or when this condition has continued, that a backflow is present.

13. A blood pump system which comprises:
a housing having an inlet port and an outlet port;
a rotor rotated in said housing for pumping blood;
a motor for rotating said rotor;
motor current measuring means for measuring motor current;
backflow detecting means for detecting a backflow of blood by use of a motor current value continuously measured by said motor current measuring means; and
wherein said backflow detecting means comprises a motor current derivative calculation means for calculating a derivative by use of the motor current value sequentially measured by said motor current measuring means, and a backflow generation determining means for determining, when a condition where the generation of zero points of the derivative calculated by said motor current derivative calculation means in a predetermined period of time appears repeatedly in shorter periods and longer periods is generated or when said condition has continued, that a backflow is present.

14. A blood pump system which comprises:
a housing having an inlet port and an outlet port;
a rotor rotated in said housing for pumping blood;
a motor for rotating the rotor;
motor current measuring means for measuring motor current backflow detecting means for detecting a backflow of blood by use of a motor current value continuously measured by said motor current measuring means; and
wherein said backflow detecting means comprises a motor current derivative calculation means for calculating a derivative by use of the motor current value sequentially measured by said motor current measuring means, derivative threshold storing means for storing a derivative threshold for determination, and a backflow generation determining means for determining when the derivative calculated by the motor current derivative calculation means is within said derivative threshold under predetermined conditions or when a condition where said derivative is within said derivative threshold under predetermined conditions is repeated, that a backflow is present.

* * * * *

UNITED STATES PATENT AND TRADEMARK OFFICE
CERTIFICATE OF CORRECTION

PATENT NO. : 7,160,242 B2 Page 1 of 1
APPLICATION NO. : 10/671543
DATED : January 9, 2007
INVENTOR(S) : Masamichi Yanai It is certified that error appears in the above-identified patent and that said Letters Patent is hereby corrected as shown below:

Claim 6, Column 17, Line 29:  insert --,-- after the word "thereof".

Claim 14, Column 20, Line 17:  insert --;-- after the word "current".

Claim 14, Column 20, Line 17:  start a new paragraph beginning with the word "backflow" (should read: "backflow detecting means for detecting a backflow of blood ...").

Signed and Sealed this

Eighteenth Day of August, 2009

David J. Kappos
*Director of the United States Patent and Trademark Office*